United States Patent
Lashinski

(10) Patent No.: US 8,518,073 B2
(45) Date of Patent: Aug. 27, 2013

(54) ILLUMINATED INTRAVASCULAR BLOOD FILTER

(75) Inventor: Randall T. Lashinski, Windsor, CA (US)

(73) Assignee: Claret Medical, Inc., Santa Rosa, CA (US)

(*) Notice: Subject to any disclaimer, the term of this patent is extended or adjusted under 35 U.S.C. 154(b) by 640 days.

(21) Appl. No.: 12/696,926

(22) Filed: Jan. 29, 2010

(65) Prior Publication Data
US 2010/0191276 A1 Jul. 29, 2010

Related U.S. Application Data

(60) Provisional application No. 61/148,054, filed on Jan. 29, 2009.

(51) Int. Cl.
*A61M 29/00* (2006.01)

(52) U.S. Cl.
USPC .................................................. 606/200

(58) Field of Classification Search
USPC ................ 606/108, 200; 623/1.11; 600/585
See application file for complete search history.

(56) References Cited

U.S. PATENT DOCUMENTS

| | | |
|---|---|---|
| 3,472,230 A | 10/1969 | Fogarty |
| 4,619,246 A | 10/1986 | Molgaard-Nielsen et al. |
| 4,650,466 A | 3/1987 | Luther |
| 4,706,671 A | 11/1987 | Weinrib |
| 4,723,549 A | 2/1988 | Wholey et al. |
| 4,873,978 A | 10/1989 | Ginsburg |
| 5,108,419 A | 4/1992 | Reger |
| 5,192,286 A | 3/1993 | Phan |
| 5,662,671 A | 9/1997 | Barbut et al. |
| 5,707,389 A | 1/1998 | Louw et al. |
| 5,766,151 A * | 6/1998 | Valley et al. ............ 604/103.07 |
| 5,779,716 A | 7/1998 | Cano et al. |
| 5,814,064 A | 9/1998 | Daniel |
| 5,827,324 A | 10/1998 | Cassell |
| 5,848,964 A | 12/1998 | Samuels |
| 5,935,139 A | 8/1999 | Bates |
| 5,980,555 A * | 11/1999 | Barbut et al. ................. 606/200 |
| 5,993,469 A | 11/1999 | McKenzie et al. |
| 6,001,118 A | 12/1999 | Daniel |

(Continued)

FOREIGN PATENT DOCUMENTS

| | | |
|---|---|---|
| DE | 10049812 | 4/2002 |
| EP | 1400257 A2 | 3/2004 |

(Continued)

OTHER PUBLICATIONS

Lashinski, Randall; U.S. Appl. No. 12/689,997 entitled "Intravascular Blood Filter," filed Jan. 19, 2010.

(Continued)

*Primary Examiner* — Gary Jackson
*Assistant Examiner* — Jonathan Hollm
(74) *Attorney, Agent, or Firm* — Knobbe Martens Olson & Bear LLP

(57) ABSTRACT

Disclosed is a novel filter and delivery means. The device described within will not interfere with standard practice and tools used during standard surgical procedures and tools such as cannulas, clamps or dissection instruments including valve replacement sizing gauges or other surgical procedures where the patient must be put on a heart-lung machine cross-clamping the aorta.

11 Claims, 27 Drawing Sheets

(56) References Cited

U.S. PATENT DOCUMENTS

| | | | |
|---|---|---|---|
| 6,027,520 | A | 2/2000 | Tsugita et al. |
| 6,042,598 | A | 3/2000 | Tsugita et al. |
| 6,083,239 | A * | 7/2000 | Addis .................... 606/200 |
| 6,096,053 | A | 8/2000 | Bates |
| 6,120,494 | A * | 9/2000 | Jonkman ................. 604/506 |
| 6,142,987 | A | 11/2000 | Tsugita |
| 6,152,946 | A | 11/2000 | Broome et al. |
| 6,171,328 | B1 | 1/2001 | Addis |
| 6,179,851 | B1 | 1/2001 | Barbut et al. |
| 6,235,045 | B1 | 5/2001 | Barbut et al. |
| 6,245,088 | B1 | 6/2001 | Lowery |
| 6,245,089 | B1 | 6/2001 | Daniel |
| 6,264,663 | B1 | 7/2001 | Cano |
| 6,270,513 | B1 | 8/2001 | Tsugita et al. |
| 6,325,815 | B1 | 12/2001 | Kusleika et al. |
| 6,336,934 | B1 | 1/2002 | Gilson et al. |
| 6,346,116 | B1 | 2/2002 | Brooks et al. |
| 6,361,545 | B1 | 3/2002 | Macoviak et al. |
| 6,371,971 | B1 * | 4/2002 | Tsugita et al. ............. 606/200 |
| 6,485,502 | B2 | 11/2002 | Don Michael et al. |
| 6,558,356 | B2 | 5/2003 | Barbut |
| 6,605,102 | B1 | 8/2003 | Mazzocchi et al. |
| 6,620,148 | B1 | 9/2003 | Tsugita |
| 6,663,652 | B2 | 12/2003 | Daniel et al. |
| 6,676,682 | B1 | 1/2004 | Tsugita et al. |
| 6,712,835 | B2 | 3/2004 | Mazzocchi |
| 6,726,651 | B1 * | 4/2004 | Robinson et al. ......... 604/101.01 |
| 6,726,701 | B2 | 4/2004 | Gilson et al. |
| 6,740,061 | B1 | 5/2004 | Oslund et al. |
| 6,843,798 | B2 | 1/2005 | Kusleika et al. |
| 6,872,216 | B2 | 3/2005 | Daniel |
| 6,887,258 | B2 | 5/2005 | Denison et al. |
| 6,905,490 | B2 | 6/2005 | Parodi |
| 7,048,752 | B2 | 5/2006 | Mazzocchi |
| 7,094,249 | B1 | 8/2006 | Broome et al. |
| 7,160,255 | B2 | 1/2007 | Saadat |
| 7,169,165 | B2 | 1/2007 | Belef et al. |
| 7,214,237 | B2 | 5/2007 | Don Michael et al. |
| 7,323,001 | B2 | 1/2008 | Clubb et al. |
| 7,410,491 | B2 | 8/2008 | Hopkins |
| 7,493,154 | B2 | 2/2009 | Bonner et al. |
| 7,559,925 | B2 | 7/2009 | Goldfarb et al. |
| 7,922,732 | B2 | 4/2011 | Mazzocchi et al. |
| 2001/0041858 | A1 * | 11/2001 | Ray et al. ................. 604/93.01 |
| 2002/0055767 | A1 | 5/2002 | Forde et al. |
| 2002/0077596 | A1 | 6/2002 | McKenzie et al. |
| 2002/0095172 | A1 | 7/2002 | Mazzocchi et al. |
| 2002/0123naturally | A1 | 9/2002 | Barbut et al. |
| 2003/0100919 | A1 | 5/2003 | Hopkins et al. |
| 2003/0171770 | A1 | 9/2003 | Kusleika et al. |
| 2004/0064092 | A1 * | 4/2004 | Tsugita et al. ............. 604/101.04 |
| 2004/0093015 | A1 * | 5/2004 | Ogle .................... 606/200 |
| 2004/0215167 | A1 | 10/2004 | Belson |
| 2004/0220611 | A1 | 11/2004 | Ogle |
| 2004/0254601 | A1 | 12/2004 | Eskuri |
| 2004/0254602 | A1 | 12/2004 | Lehe et al. |
| 2005/0010285 | A1 * | 1/2005 | Lambrecht et al. .......... 623/2.18 |
| 2005/0080356 | A1 | 4/2005 | Dapolio et al. |
| 2005/0101987 | A1 | 5/2005 | Salahieh |
| 2005/0137696 | A1 | 6/2005 | Salahieh |
| 2006/0015136 | A1 | 1/2006 | Besselink |
| 2006/0015138 | A1 * | 1/2006 | Gertner .................... 606/200 |
| 2006/0030877 | A1 | 2/2006 | Martinez et al. |
| 2006/0100658 | A1 | 5/2006 | Obana et al. |
| 2006/0129180 | A1 | 6/2006 | Tsugita et al. |
| 2006/0161241 | A1 | 7/2006 | Barbut et al. |
| 2006/0259066 | A1 | 11/2006 | Euteneuer |
| 2008/0004687 | A1 | 1/2008 | Barbut et al. |
| 2008/0058860 | A1 | 3/2008 | Demond et al. |
| 2008/0065145 | A1 | 3/2008 | Carpenter |
| 2008/0065147 | A1 | 3/2008 | Mazzocchi et al. |
| 2008/0125848 | A1 | 5/2008 | Kusleika et al. |
| 2008/0188884 | A1 | 8/2008 | Gilson et al. |
| 2008/0234722 | A1 | 9/2008 | Bonnette et al. |
| 2008/0262442 | A1 | 10/2008 | Carlin et al. |
| 2009/0024153 | A1 | 1/2009 | Don Michael |
| 2009/0069840 | A1 | 3/2009 | Hallisey |
| 2009/0198269 | A1 | 8/2009 | Hannes et al. |
| 2009/0203962 | A1 | 8/2009 | Miller et al. |
| 2009/0326575 | A1 | 12/2009 | Galdonik et al. |
| 2010/0004633 | A1 | 1/2010 | Rothe et al. |
| 2010/0063537 | A1 | 3/2010 | Ren et al. |
| 2010/0179583 | A1 | 7/2010 | Carpenter et al. |
| 2010/0179584 | A1 | 7/2010 | Carpenter et al. |
| 2010/0179585 | A1 | 7/2010 | Carpenter et al. |
| 2010/0179647 | A1 | 7/2010 | Carpenter et al. |
| 2010/0185231 | A1 | 7/2010 | Lashinski |
| 2010/0191276 | A1 | 7/2010 | Lashinski |
| 2010/0211095 | A1 | 8/2010 | Carpenter |
| 2010/0312268 | A1 | 12/2010 | Belson |
| 2010/0324589 | A1 | 12/2010 | Carpenter et al. |
| 2011/0022076 | A1 | 1/2011 | Lashinski |
| 2011/0066221 | A1 | 3/2011 | White et al. |
| 2011/0282379 | A1 | 11/2011 | Lee et al. |

FOREIGN PATENT DOCUMENTS

| | | |
|---|---|---|
| EP | 1253871 | 2/2007 |
| WO | WO 2008/100790 A2 | 8/2008 |
| WO | WO 2010083527 A2 | 7/2010 |
| WO | WO 2010/088520 A2 | 8/2010 |
| WO | WO 2011/034718 A2 | 3/2011 |
| WO | WO 2011/017103 A2 | 10/2011 |
| WO | PCT/US2011/067598 | 12/2011 |

OTHER PUBLICATIONS

Lashinski, Randall; U.S. Appl. No. 12/844,420 entitled "Dual Endovascular Filter and Methods of Use," filed Jul. 27, 2010.

Lee et al.; U.S. Appl. No. 12/871,708 entitled "Intravascular Blood Filters and Methods of Use," filed Aug. 30, 2010.

International Search Report in Application No. PCT/US2010/021417 dated Aug. 23, 2010, in 4 pages.

International Search Report in Application No. PCT/US2010/047166 dated Apr. 27, 2011, in 7 pages.

International Search Report in Application No. PCT/US2010/043390 dated Apr. 8, 2011, in 11 pages.

International Search Report in Application No. PCT/US2011/067598 dated May 10, 2012, in 45 pages.

International Preliminary of Patentability in Application No. PCT/US2010/022590 dated Jan. 29, 2010, in 4 pages.

* cited by examiner

ILLUMINATED INTRAVASCULAR BLOOD FILTER

CROSS REFERENCE TO RELATED APPLICATIONS

This application claims the benefit under 35 U.S.C. 119 of U.S. Provisional Patent Application No. 61/148,054, filed Jan. 29, 2009, titled "Illuminated Intravascular Blood Filter." This application is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

This invention relates generally to medical devices used during vascular intervention, and more particularly, concerns medical devices that are useful in treating aortic valve replacement, thromboembolic disorders and for removal of foreign bodies in the vascular system.

Thromboembolic disorders, such as stroke, pulmonary embolism, peripheral thrombosis, atherosclerosis, and the like, affect many people. These disorders are a major cause of morbidity and mortality in the United States and throughout the world. Thromboembolic events are characterized by an occlusion of a blood vessel. The occlusion can be caused by a clot which is viscoelastic (jelly-like) and is comprised of platelets, fibrinogen, and other clotting proteins.

Percutaneous aortic valve replacement has been in development for some time now and stroke rates related to this procedure are between four and twenty percent. During catheter delivery and implantation plaque may be dislodged from the vasculature. The invention contained within will block the emboli from traveling through the carotid circulation and onto the brain. When an artery is occluded by a clot, tissue ischemia (lack of oxygen and nutrients) develops. The ischemia will progress to tissue infarction (cell death) if the occlusion persists. Infarction does not develop or is greatly limited if the flow of blood is reestablished rapidly. Failure to reestablish blood-flow can lead to the loss of limb, angina pectoris, myocardial infarction, stroke, or even death.

Occlusion of the venous circulation by thrombi leads to blood stasis which can cause numerous problems. The majority of pulmonary embolisms are caused by emboli that originate in the peripheral venous system. Reestablishing blood flow and removal of the thrombus is highly desirable.

There are many existing techniques employed to reestablish blood flow in an occluded vessel. One common surgical technique, an embolectomy, involves incising a blood vessel and introducing a balloon-tipped device (such as a Fogarty catheter) to the location of the occlusion. The balloon is then inflated at a point beyond the clot and used to translate the obstructing material back to the point of incision. The obstructing material is then removed by the surgeon. While such surgical techniques have been useful, exposing a patient to surgery may be traumatic and is best avoided when possible. Additionally, the use of a Fogarty catheter may be problematic due to the possible risk of damaging the interior lining of the vessel as the catheter is being withdrawn.

A common percutaneous technique is referred to as balloon angioplasty where a balloon-tipped catheter is introduced into a blood vessel, typically through an introducing catheter. The balloon-tipped catheter is then advanced to the point of the occlusion and inflated in order to dilate the stenosis. Balloon angioplasty is appropriate for treating vessel stenosis but is generally not effective for treating acute thromboembolisms.

Another percutaneous technique is to place a microcatheter near the clot and infuse Streptokinase, Urokinase, or other thrombolytic agents to dissolve the clot. Unfortunately, thrombolysis typically takes hours to days to be successful. Additionally, thrombolytic agents can cause hemorrhage and in many patients the agents cannot be used at all.

Another problematic area is the removal of foreign bodies. Foreign bodies introduced into the circulation can be fragments of catheters, pace-maker electrodes, guide wires, and erroneously placed embolic material such as thrombogenic coils. There exist retrieval devices for the removal of foreign bodies, certain of such devices form a loop that can ensnare the foreign material by decreasing the size of the diameter of the loop around the foreign body. The use of such removal devices can be difficult and sometimes unsuccessful.

Moreover, systems heretofore disclosed in the art are generally limited by size compatibility and the increase in vessel size as the emboli is drawn out from the distal vascular occlusion location to a more proximal location near the heart. If the embolectomy device is too large for the vessel it will not deploy correctly to capture the clot or foreign body, and if too small in diameter it cannot capture clots or foreign bodies across the entire cross section of the blood vessel. Additionally, if the embolectomy device is too small in retaining volume then as the device is retracted the excess material being removed can spill out and be carried by flow back to occlude another distal vessel.

Various thrombectomy and foreign matter removal devices have been disclosed in the art. However, such devices have been found to have structures which are either highly complex or lacking in sufficient retaining structure. Disadvantages associated with the devices having highly complex structure include difficulty in manufacturability as well as difficulty in use in conjunction with microcatheters. Recent developments in the removal device art features umbrella filter devices having self folding capabilities. Typically, these filters fold into a pleated condition, wherein the pleats extend radially and can obstruct retraction of the device into the microcatheter sheathing.

What has been needed and heretofore unavailable is an extraction device that can be easily and controllably deployed into and retracted from the circulatory system for the effective removal of clots and foreign bodies. There is also a need for a system that can be used as a temporary arterial or venous filter to capture and remove thromboemboli generated during endovascular procedures. Moreover, due to difficult-to-access anatomy such as the cerebral vasculature and the neurovasculature, the invention should possess a small collapsed profile and preferably be expandable to allow the device to be delivered through the lumen of commercially available catheters. The present invention satisfies these needs.

SUMMARY OF THE INVENTION

Most filter devices are delivered from the groin and are placed distal to the flow of the lesion or site in question. Single basket-type filters or Nitinol loop filters are the most common used today in carotid stent procedures of vein graft stenting. As the guidewire is delivered past the lesion the filter is delivered over the guidewire protecting the distal vasculature. The invention here will be delivered in an open surgical procedure where the heart is put onto heart-lung bypass. In this operation, the surgeon will open the chest cavity exposing the heart for direct visualization. Normally cannulas are placed into main vessels to continue circulation and the aorta is cross-clamped to eliminate flow to the heart. This will allow the surgeon to access the heart and heart valves for replacement or repair without excessive bleeding. During the process of cross-clamping the aorta may shed internal particulate such as plaque or calcium deposits that have collected along the inner wall. This particulate may travel downstream and cause obstruction to distal vessels starving them of oxygenated blood and the surrounding tissue may die quickly without proper blood flow. This is inclusive of the brain where occlusion of these vessels is referred to as a stroke. The main vessels feeding the brain are the carotid arteries and the initiate from the aortic arch. Filters have been developed for catheterization procedures where the filter is placed proximal to the placement of a stent in the carotid artery. These are guided by fluoroscopy as the devices inserted into the vessels are radiopaque and are displayed a dark objects on a display screen. This could be possible for a surgical procedure but it would add another step in the process by admitting the patient to the catheterization lab and placing a filter in each carotid artery. This would add to the complexity of the procedure and also add additional cost to the hospital and patient. The invention disclosed here would allow the surgeon to place the device in a beating heart where the insertion could be at the access for the aortic cannula. Placement of these devices could be guided by fluoroscopy or echo but the preferred method would be to utilize an illumination of the device being delivered. One method of illumination would be to utilize the guidewire as an optical fiber with an external light source to deliver photons to the distal portion of the catheter or an internal light emitting diode (LED) mounted to the distal portion of the device where the surgeon could visualize the advancement and deployment of the device in to the carotid arteries by seeing the light source through the vessel wall. A standard purse-string suture would be tied before cannula insertion and the filters would be inserted first and positioned into the carotid vessels. By illuminating a portion of the device, visual guidance of the filters through the vessel wall is possible. Once the filters are in placed the cannula may be inserted with the carotid arteries protected from emboli and perfusion and cross-clamping may begin. The surgeon may now perform the normal operation such as valve repair or replacement, coronary artery bypass with embolic protection in place. The cross-clamping would not be effected due to the very small (0.010 to 0.035 inch) filter wires in place. Once the operation is completed, recovery of these wires can occur under normal flow and perfusion. They may be recovered before the cross-clamp is removed or after the heart is recovered and beating normally. The later may provide a safer approach as emboli may still be shed from the removal and trauma to the aortic vessel.

The above described illumination guidance technique could be substituted with a magnetic source at the distal portion of the filter device or guidewire and externally located within the aorta with a wand to attract the filter via magnetic field. This would allow the filter to be pulled into the carotid vessels under direct visualization externally via two magnetic sources.

One method of filtering the carotid arteries leaving the aorta free from obstruction is to deliver a filter to each of the carotid arteries from the groin leaving them in the carotid vasculature and retrieving them via snare post procedure. A delivery catheter would be inserted through an introducer in the groin (femoral artery) and delivered to the common carotid arteries and detached. The delivery catheter would be removed and a second filter would be delivered in a similar manner to the other carotid artery. With two detached filters now in place the procedure treating the aortic or mitral valve can now be completed with embolic protection for the cerebral vascular system. Once the procedure to the valve is completed, the filters can be snared and retrieved back out the femoral artery as they were delivered. Any embolic particles will be captured in the filter device and removed safely from the body.

Another method for filtering the carotid arteries would be to deliver a filter from the femoral artery and utilize a single catheter to house the two attachment means to the filters. These attachments may be a wire similar to a guidewire or a hypo-tube to connect the filter element to an external portion of the body. Keeping these wires or connection means organized and contained within a single or dual lumen catheter will help organize and limit potential entanglement with other catheters being delivered to the target site such as the aortic valve or other cardiac elements including but not limited to the mitral valve and coronary arteries. The distal portion of the catheter may have a single exit portion or a staggered exit to allow an exit at different points along the catheter. One exit port may be at the distal most end of the catheter and the other may be a centimeter proximal from this to allow the attachment wire to exit near the left common carotid artery. Furthermore, there could be an extension to the distal most portion of the catheter allowing side ports for both wires to exit. This would allow for additional catheter stabilization within the aorta.

Another embodiment would deliver filters to the carotid from the radial artery and allow for a clear aortic arch from catheters and other delivery means from a more conventional femoral delivery means. From this access site a plurality of filters could be delivered through a common access sheath or the filters could be delivered from a dual lumen catheter with each lumen housing a single filter.

Another delivery means would utilize a single catheter with filters mounted in a coaxial manner where the distal filter would be delivered first and could be mounted to a wire where the second would be mounted to a hypo-tube where the first filters wire would run through the second allowing for relative motion between the two filters. The first filter would be delivered to the left common carotid from the radial artery and the second would be delivered to the right common carotid artery or the brachiocephalic trunk in a coaxial manner. These filters would be opposed in direction as the distal filter would be filtering blood flowing from the base of the aorta to the head and toward the distal end of the guidewire. The proximal filter would be filtering blood from the base of the aorta to the head and toward the proximal end of the guidewire. Placing the two filters together there would be a conical shape configuration where the large diameter portions of the cones would meet. These two filters would be delivered in a collapsed configuration and expanded when expelled from the delivery catheter. Retrieval would be a retraction of the filter back into a recovery catheter that would be a larger inner diameter than the delivery catheter to allow room for particulate. Being opposed in capture direction the right carotid would be the first filter that would be recovered by an expanded sheath where the embolic material would not be disturbed and further withdrawn to a smaller sheath for removal from the body. The expanded sheath could be constructed from braided Nitinol wire pre-shaped so when exposed the braid would expand to receive the filter without squeezing out any trapped emboli.

The second or left carotid filter would be recovered in a conventional manner where the larger diameter would be pulled into a sheath to trap and remove the emboli within the tail or distal portion of the filter.

Another means to deliver the filters via radial artery approach would be to utilize a dual lumen catheter where each lumen would house a single filter. The first lumen would deliver a filter to the left carotid artery and the second lumen would deliver a filter to the right carotid artery. The lumens could be staggered in length to reach each ostium in which case the first or left filter lumen would be longer in length to allow for placement distal from the second filter placement in the right carotid. Additionally, the second lumen may be pre-shaped with a curve to allow easy access to the right carotid artery. This pre-shaped curve may be retained in a straighter manner to allow for delivery and released to express the delivery shape when at the bifurcation of the subclavian and the carotid artery. Furthermore, there may be an active shaping where the curve is directed external to the body by a handle mechanism such as a pull-wire where tension would generate a compressive force to the catheter column preferentially bending the lumen. Recovery could utilize the same dual lumen concept or utilize a second recovery sheath independently from one another.

Another application for this device and method would be for surgical operations where the patient may be put on heart-lung bypass. During cross clamping of the aorta catheters or wires in the aorta may interfere with the procedure and allow leakage of blood around the cannulas used. If any of the above described devices or techniques are used before the patient's chest is opened this filtration of the carotid vessels would protect from emboli thus reducing the stroke risk during and after the procedure. Additional antithrombotic coatings to the filter could allow for an extended implantation time allowing filtration time to be extended post procedure. An example of this coating would be Heparin. Placement of these catheters and filters could be under fluoroscopy or ultrasound guidance to direct proper filter placement. Radiopaque markers may add necessary visibility to the catheter, filter and or wires.

Another surgical delivery means would be an insertion to the carotid artery via the neck. The filter could face either antigrade or retrograde depending upon the placement insertion point or access site. This would allow for complete filtration without any aortic interference as the entire devices would be within the carotid circulation. With this delivery technique the puncture site would be very small and recovery could be through the entry site or through the groin as the filter could be inserted distal to meet a recovery sheath in the aorta. With this groin recovery any emboli within the proximal carotid would be captured before later dislodgement.

Intravascular filters have been used in many configurations ranging from a windsock style as commercialized as the FilterWire from Boston Scientific or the ACCUNET from Abbott Vascular or the Spider from eV3. These filters utilize a memory metal such as Nitinol is used to oppose the vascular wall tightly sealing any emboli from passage while a filter material such as a porous fabric material retains and emboli from passing distally from the device. Another example is a laser cut memory metal where the basket is the frame and the filter is used to trap emboli when expanded. Another example is constructed from a braided wire such as Medtronic's Interceptor PLUS where once exposed the braid expands to create a funnel or cone shape to trap emboli and the proximal or larger end is pre-shaped to accept blood flow with larger openings heat-set into the memory metal such as Nitinol. These filters range in diameter from about 2-15 mm in diameter and are approximately 20-30 mm in length. They are generally attached to a guidewire and sheathed for delivery and resheathed for recovery. The catheter profile measures about 1 to 2 mm in diameter and has a length of about 90 to 200 cm. Catheter construction is normally a polypropylene or polyethylene material but nylons and blends can be used as well. All devices are considered single use and are commonly placed for carotid stenting or savenous veign grafts stenting.

Another means of filtering the carotid arteries would be to utilize the radial artery for entry to the vasculature with an introducer. The nominal size vessel would accept a 5 to 6 French introducer which measures about 0.092-0.118 inches in outer diameter and about 0.066-0.079 inches inner diameter. Once the vessel access has been gained a guidewire measuring between 0.010 inches and 0.035 inches could be used and can be advanced through the radial artery and farther to traverse the subclavian artery accessing the brachiocephalic trunk stemming from the aorta. Immediately adjacent is the left common artery where the guidewire would be placed for catheter advancement. A pre-shaped catheter can be advanced over this guidewire to deploy the filters. The pre-shaped curve will be used to engage the ostia of the left common carotid artery and allow advancement of the first filter to protect the left carotid circulation. Pulling the guiding catheter back out of the left carotid artery and back into the brachiocephalic trunk the second filter may be advanced out of the guiding catheter protecting the right carotid circulation. Additionally, the pre-shaped curve may be straightened by advancing a still straight wire down the lumen of the guide catheter. This wire may traverse the same lumen the filters are delivered through or a separate dedicated lumen providing a generally straight shape for re-engaging the brachiocephalic trunk in a less curved shape. Another means to change the shape of this catheter is to provide a tension wire to deflect the tip similar to an electrophysiology catheter. In which case the catheter would be deflected when engagement of the left carotid is necessary and allowed to remain straight when in the brachiocephalic trunk. The same guiding catheter used for delivery of these filters could be used for recovery where the filters are collapsed back down for removal of the embolic material from the body. Ideally the two filters would be opposed in direction and on one common guidewire where the proximal filter would be recovered first and the distal, or left carotid, filter would be recovered secondarily. Since the distal portion of the first filter would be drawn into the catheter first there is a chance for release of embolic material. It may be necessary to flare the distal tip of the guide catheter to allow the tail end of the first filter to enter into the catheter without pushing the emboli out. This flare may be achieved by a split end to the catheter, the advancement of a larger diameter tube from the inside of the catheter or a basket braided to accept a larger diameter retrieval.

DETAILED DESCRIPTION OF THE PREFERRED EMBODIMENT

Figure 1:
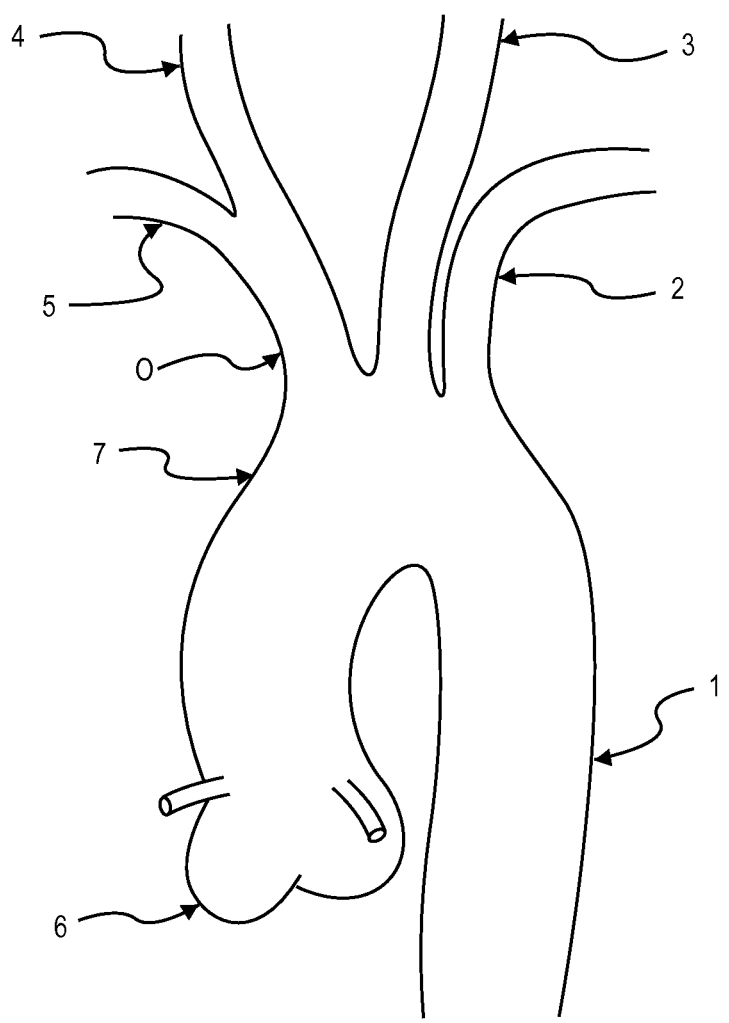
FIG. 1 illustrates the vascular anatomy of the aorta and surrounding great vessels.
Figure 2:
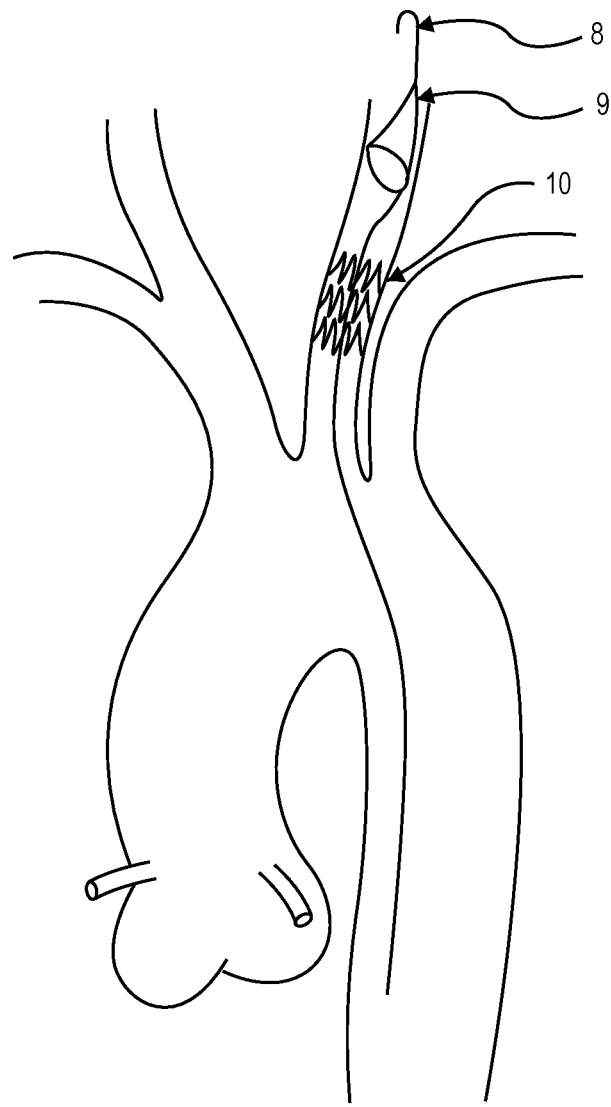
FIG. 2 illustrates the common technique in carotid filter 8 insertion for carotid stenting 10 as delivered via femoral artery over a guidewire 9.
Figure 3:
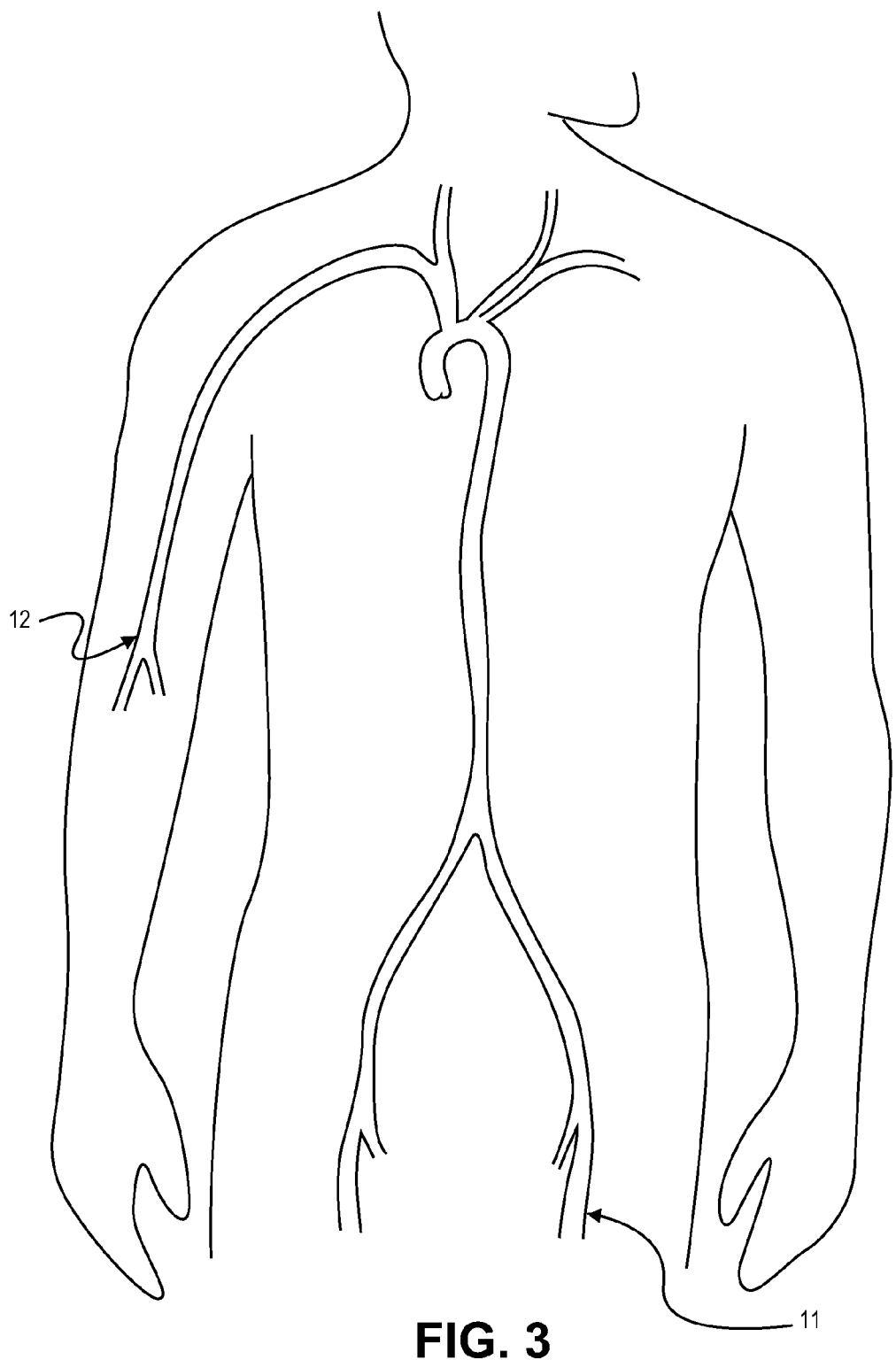
FIG. 3 illustrates the aortic vasculature where sheaths could be placed by the interventional cardiologist. The right femoral 11 being the most common access as the cardiologist works from the right side of the patient which is presented to the physician while on the table. The right radial artery 12 has been used but due to the small diameter of the vessel is not a common insertion point for the cardiologist.
Figure 4:
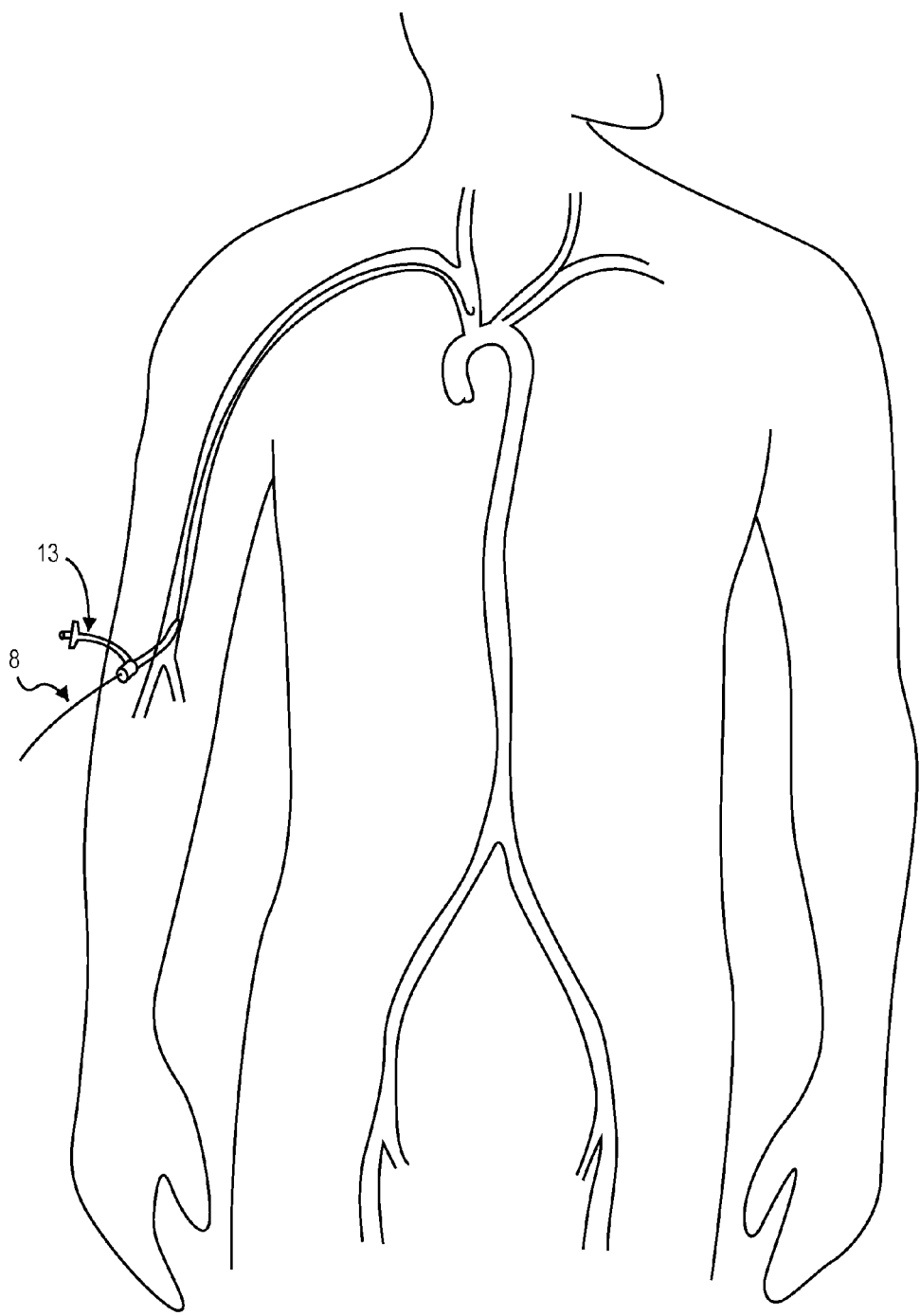
FIG. 4 illustrates a radial entry with common introducer 13 and guidewire 8 techniques.
Figure 5:
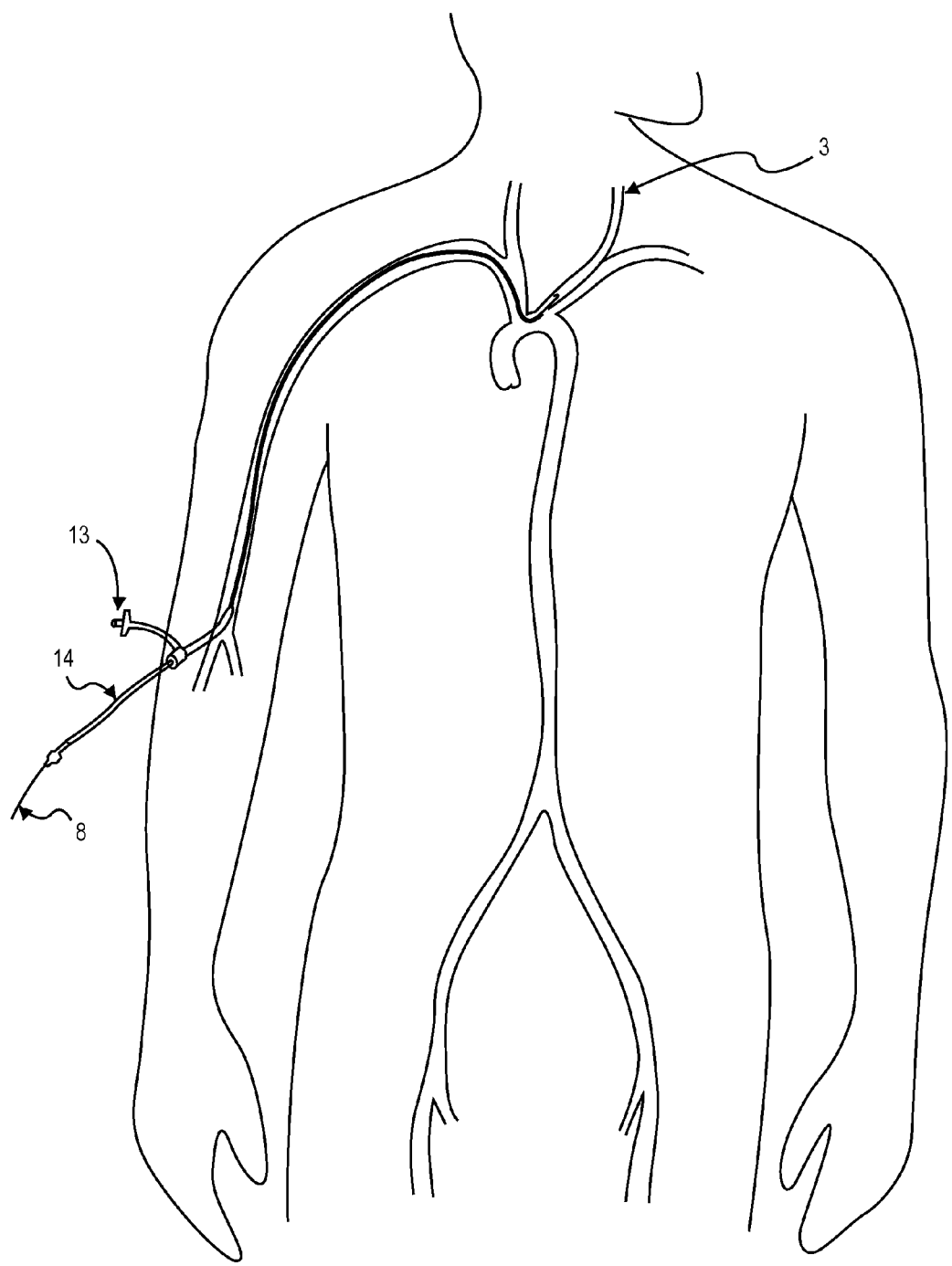
FIG. 5 illustrates the guide catheter 14 being inserted to the introducer 13 over the guidewire 8 in a radial artery entry where the guide catheter 14 has a preshaped distal section to access the left common carotid 3.
Figure 6:
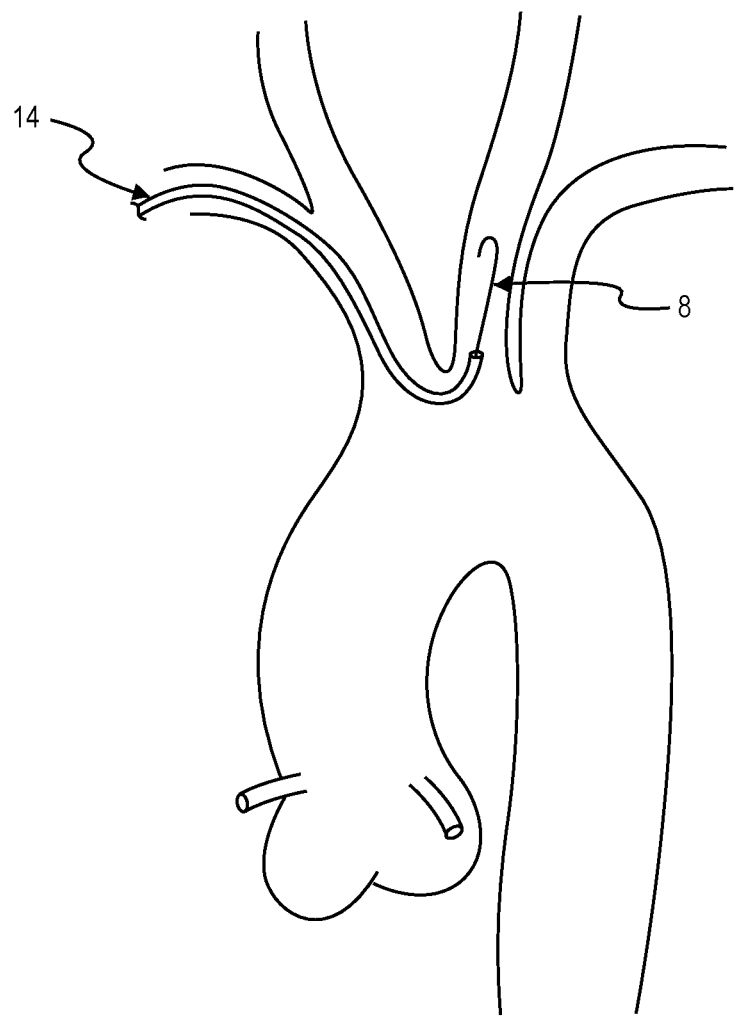
FIG. 6 illustrates a closer view of the guide catheter 14 and guidewire 8 accessing the left carotid artery where the first filter would be placed.
Figure 7:
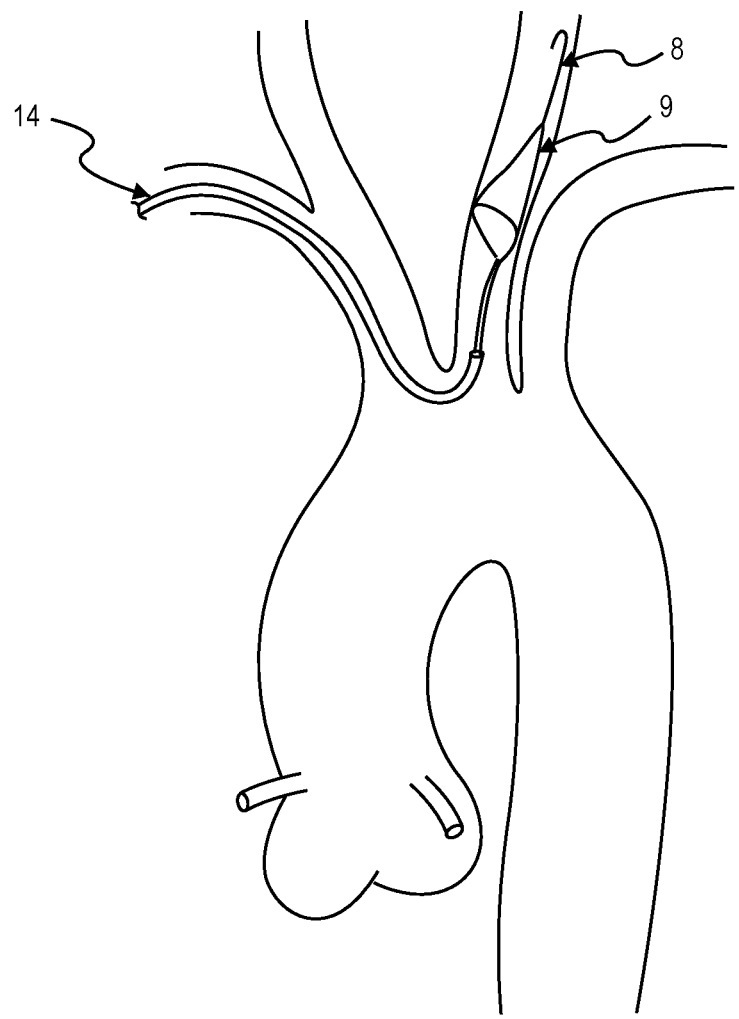
FIG. 7 illustrates the deployment of the first filter 9 through the guide catheter 14 over a guidewire 8 where the filter 9 is fully opposed to the left carotid artery.
Figure 8:
FIG. 8 illustrates both filters 9 deployed and protecting the carotid arteries utilizing a common guidewire 8 and common guide catheter 14.
Figure 9:
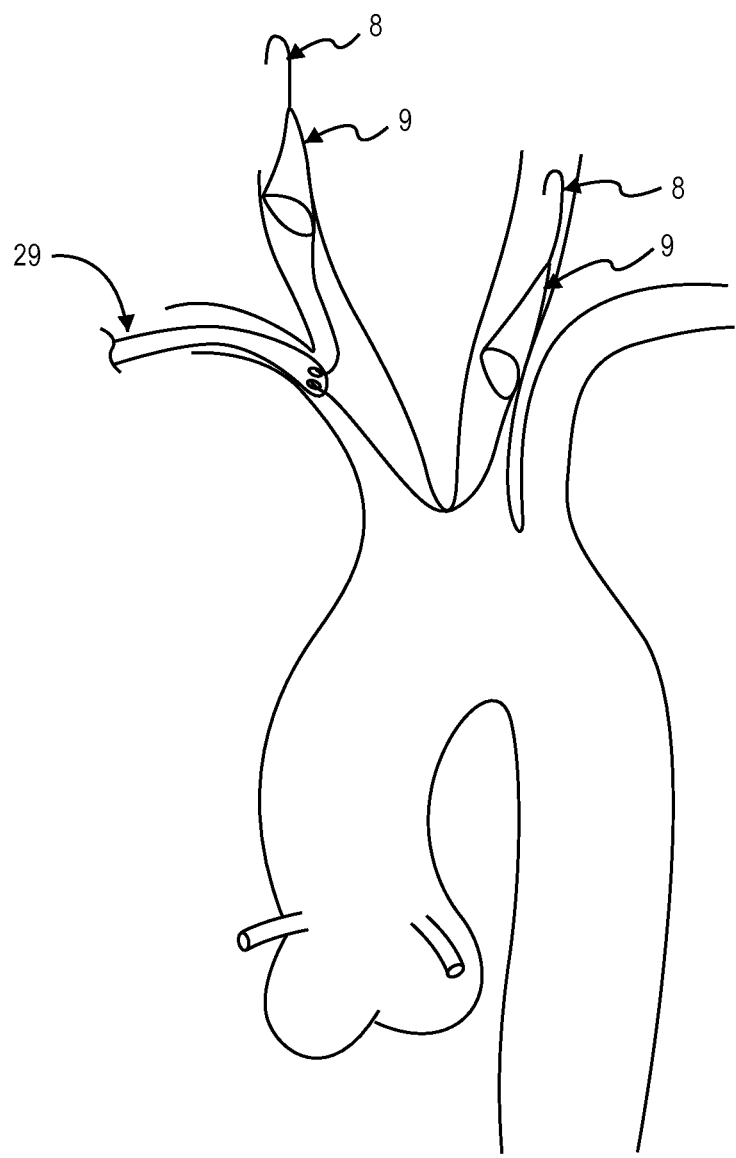
FIG. 9 illustrates a dual lumen catheter 29 where each filter 9 has a single guidewire 8. Both filters 9 are in a conventional orientation where the flow is in the distal direction or toward the distal tip of the guidewire 8. Independent recovery of the filters 9 could occur or a common recovery sheath may be used to load both into one sheath.
Figure 10:
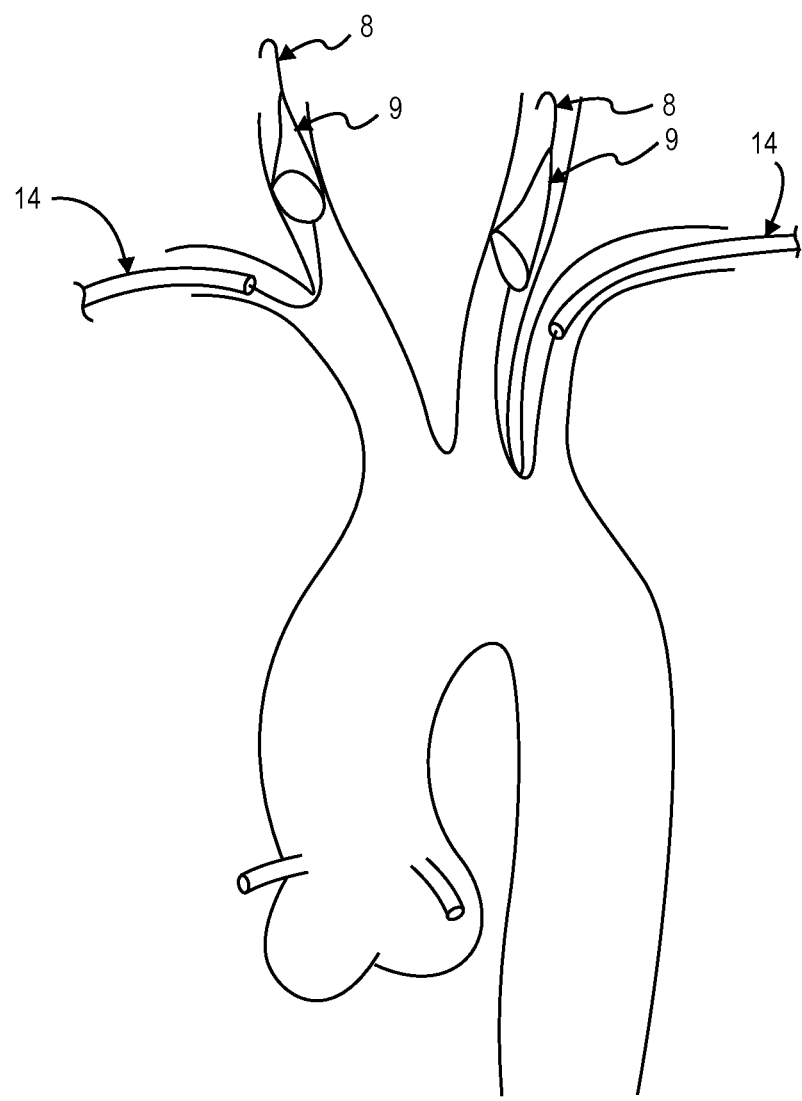
FIG. 10 illustrates both filters 9 being delivered via subclavian where the left filter is delivered via left subclavian artery with an entry point in the radial artery. Each delivery would include a guidewire 8 and a guide catheter 14 where a preshaped curve would allow access into the respective carotid artery.
Figure 11:
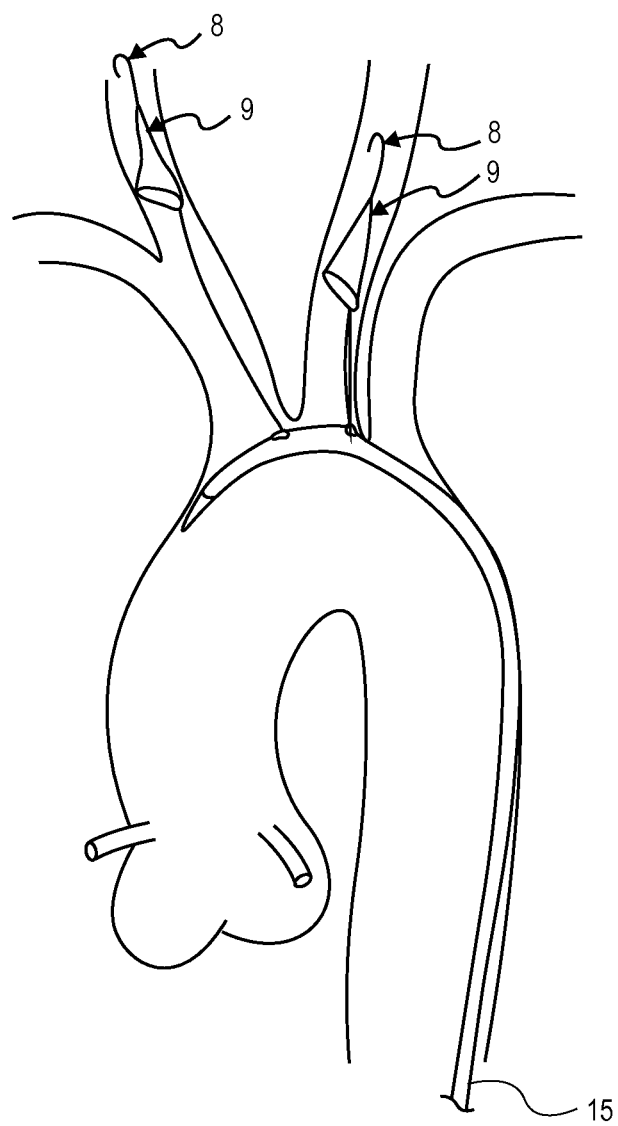
FIG. 11 illustrates a single organization catheter 15 to retain two filter 9 guidewires 8 controlling the potential for entanglement with each wire or other catheters introduced to the body. These catheters would include pigtail catheters used for contrast injections, balloon catheters for dilation or other catheters for delivery of therapeutic agents or implantable devices such as stents or prosthetic heart valves where the catheters are generally larger (18-26 French) in diameter. The catheter would have two distal exit ports to allow each filter to exit at the respective ostia. A distal section would extend beyond the brachiocephalic trunk allowing for a smooth shape to the catheter and ensure it is close to the outer radius of the arch.
Figure 12:
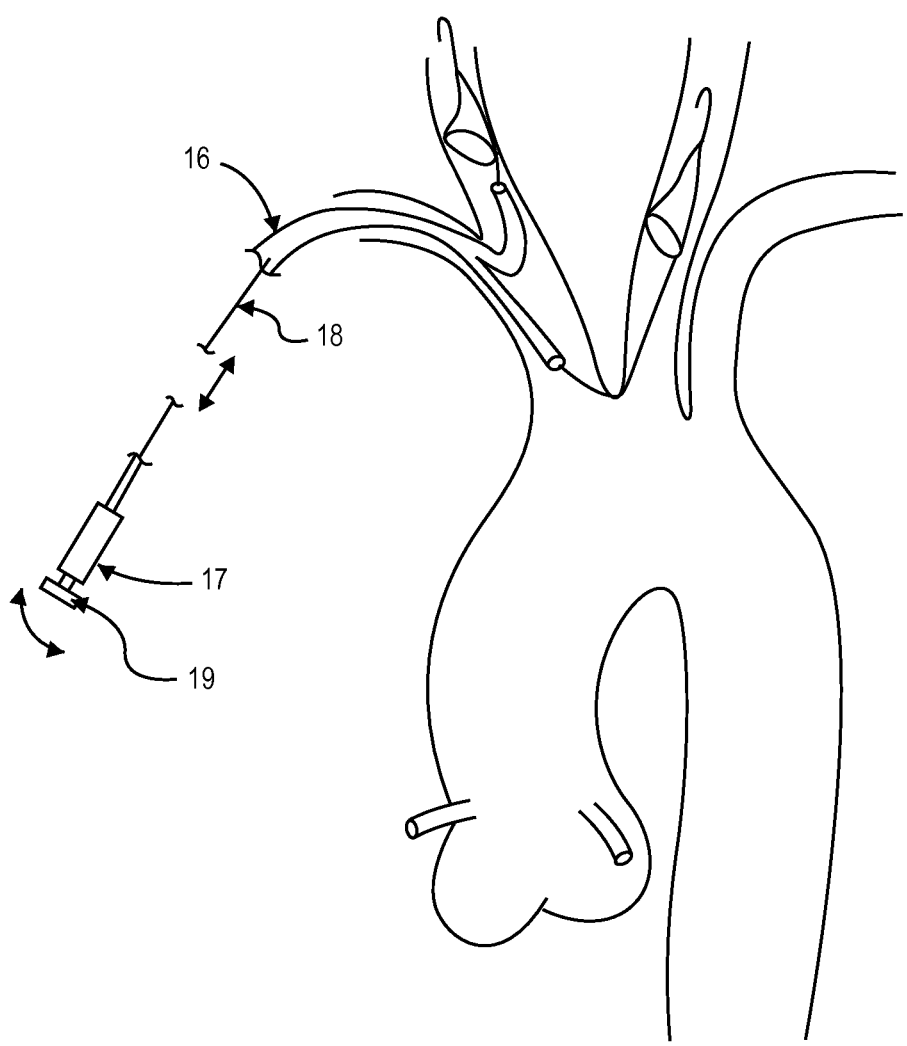
FIG. 12 illustrates a dual lumen catheter 16 with an active curving mechanism to steer each lumen to the respected carotid artery. The deflection will allow for active steering of each distal section to account for any differences in anatomy from patient to patient. Similar to electrophysiology catheters a deflection wire 18 could be tensioned to provide a bias or curve to tip. The delivery of each filter would be in a conventional orientation where the blood flow would be in the distal direction and toward the tip of the guidewire. External to the body would be a handle mechanism 17 providing an actuation force to the distal portion of the catheter. This actuation could be a rotational knob 19 translating a rotation movement to a screw mechanism providing a tension to a wire connected to the catheter tip. Other methods could include an electrical signal to drive a motion or hydraulic actuation to translate a force.
Figure 13:
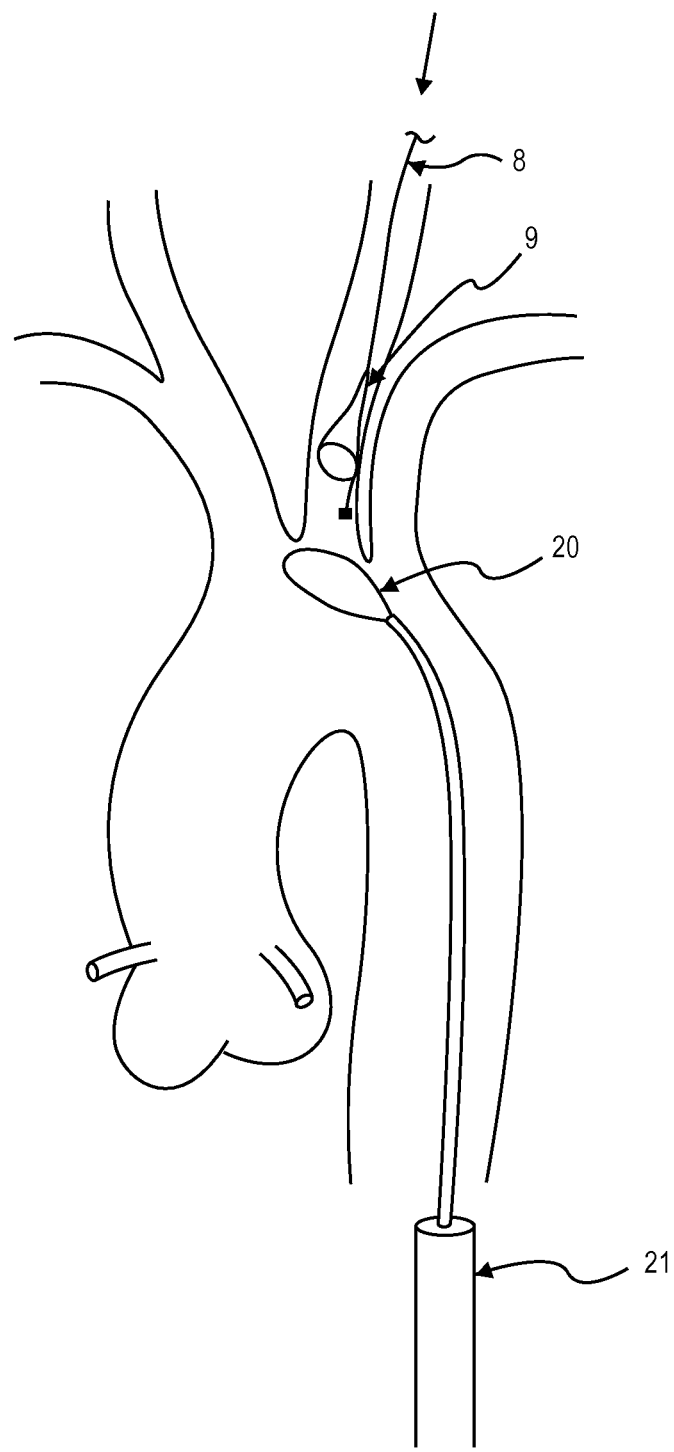
FIG. 13 illustrates a filter 9 delivered over the guidewire 8 from the carotid artery in a retrograde approach just short of the aortic arch. Once the procedure is completed the filter can be snared with a conventional snare 20 to remove it from the body. This will allow for a very small (0.03 inch) entry port in the neck to introduce the device and a larger recovery sheath 21 in the groin where other devices are introduced.
Figure 14:
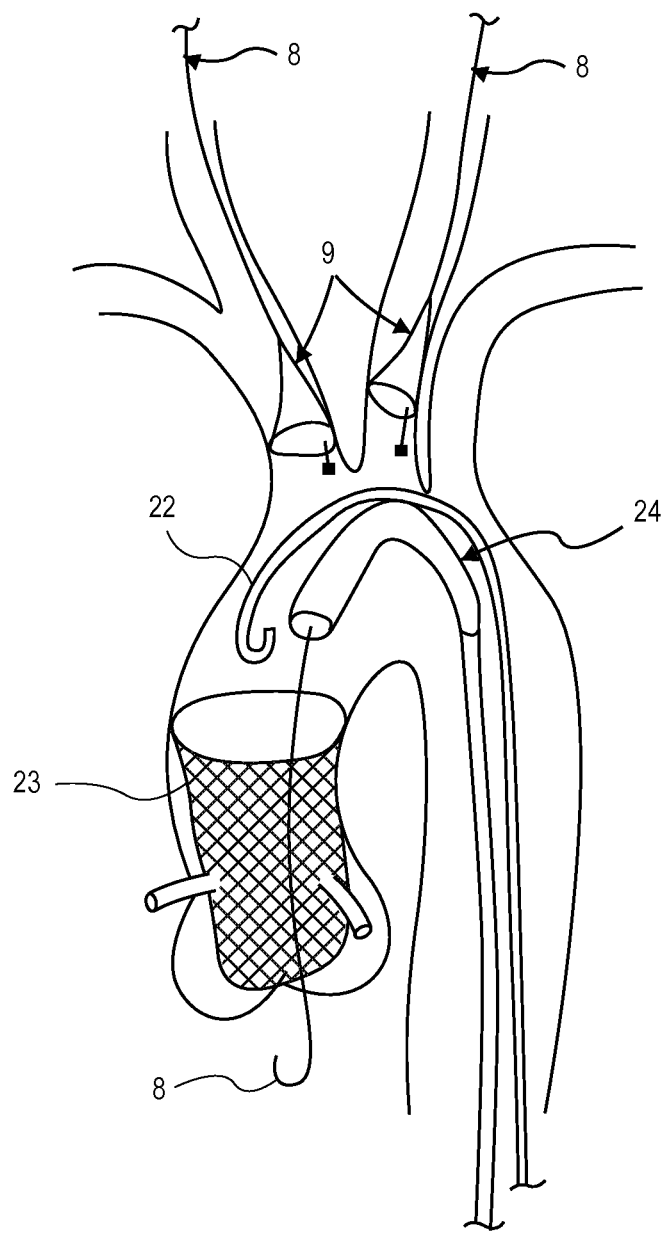
FIG. 14 illustrates a set of filters in the carotid arteries delivered and ready for additional procedures to occur under filtered protection. During a percutaneous heart valve delivery there maybe multiple catheters in the aortic arch consuming much of the available area. Shown here is a pigtail catheter 22 and a delivery catheter 24 for a percutaneous heart valve 23 all within the aortic arch. The filters 9 are clear of the aortic space and will not interfere with delivery or withdrawal of these catheters.
Figure 15:
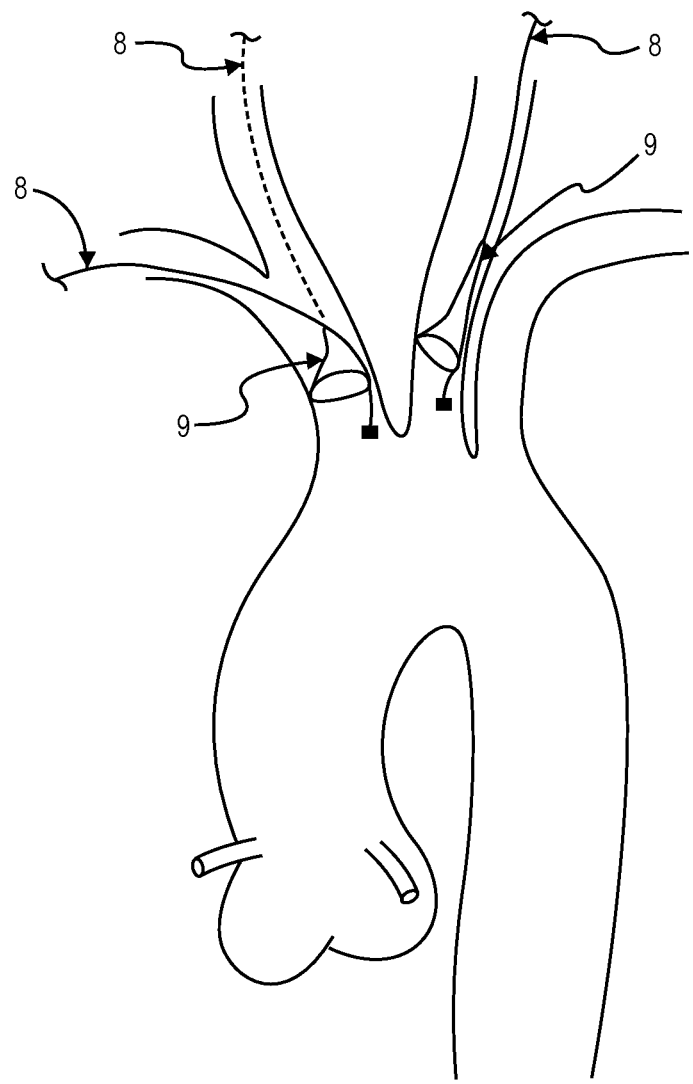
FIG. 15 illustrates another delivery pathway for the placement in the carotid or brachiocephalic trunk. Delivery includes a guidewire 8 introduced via carotid artery or subclavian artery just short of the aortic arch leaving the arch free from interference while delivering other catheters to the heart. These filters 9 can be retrieved either through the groin or recovered back through the entry point in the carotid or subclavian artery.
Figure 16:
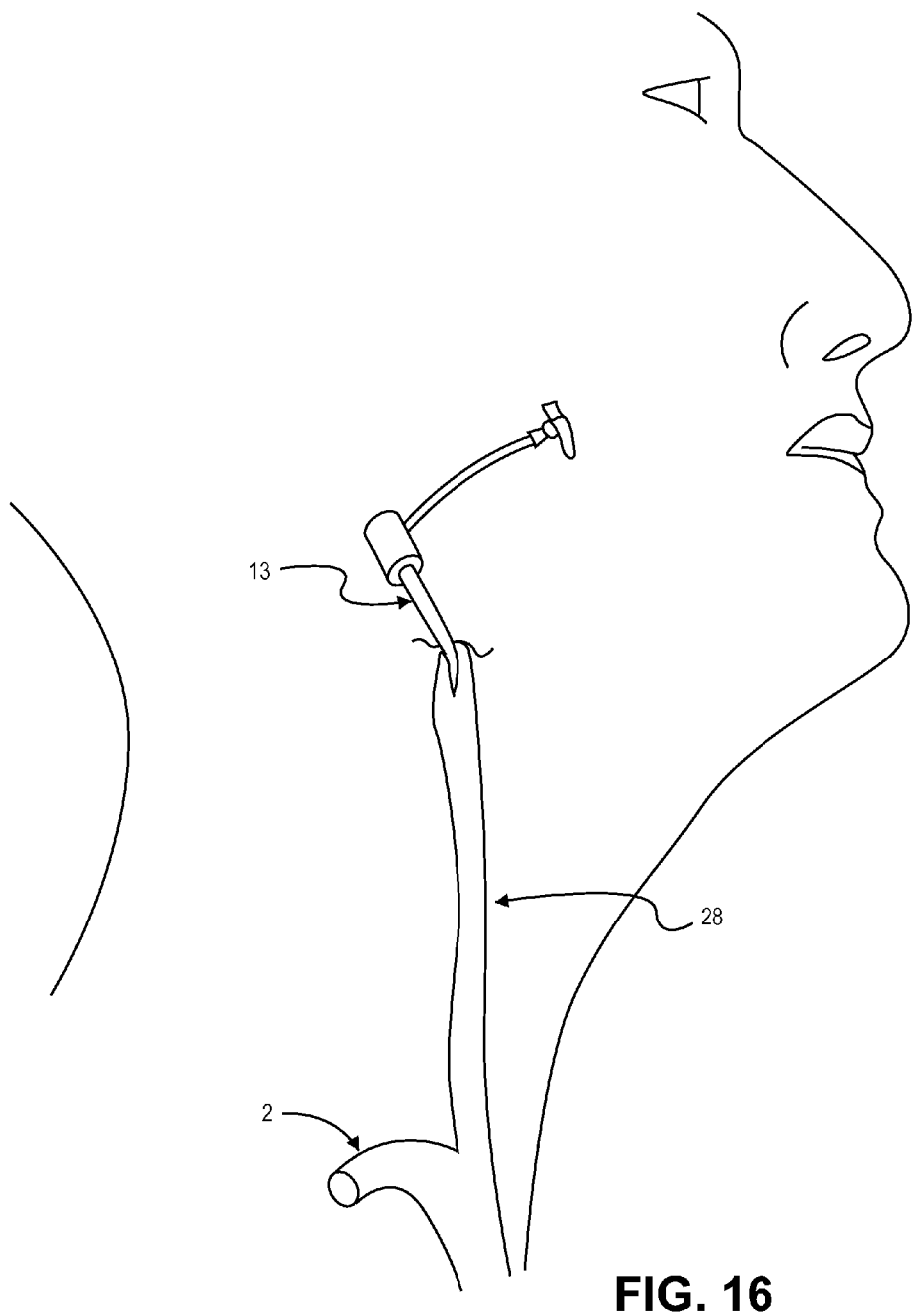
FIG. 16 illustrates a conventional entry to the carotid artery where the sheath is placed in a retrograde manner. A sheath 13 is placed into the carotid artery where access may be gained to the vasculature either antigrade or retrograde depending upon the desired placement of the device.
Figure 17:
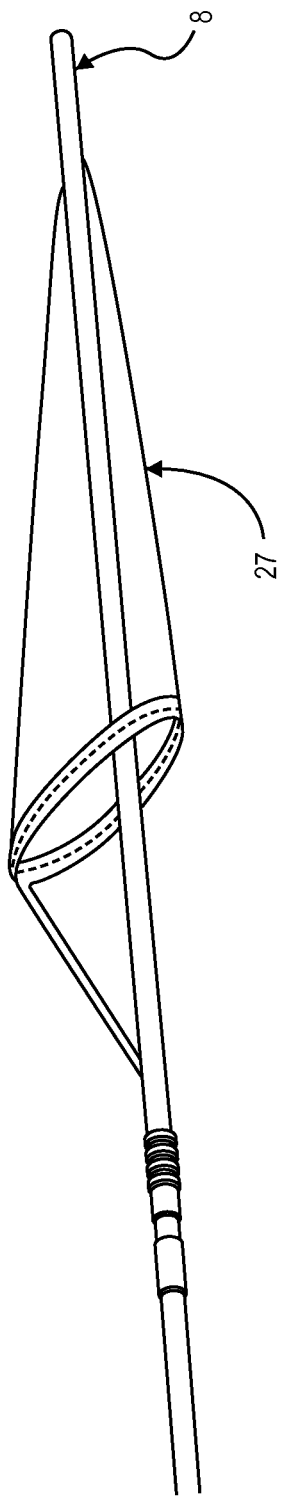
FIG. 17 illustrates an example of a common filter design where the guidewire 8 passes through the central portion of the filter 27. A memory material such as Nitinol is used to expand the filter material to the vessel wall.
Figure 18A:
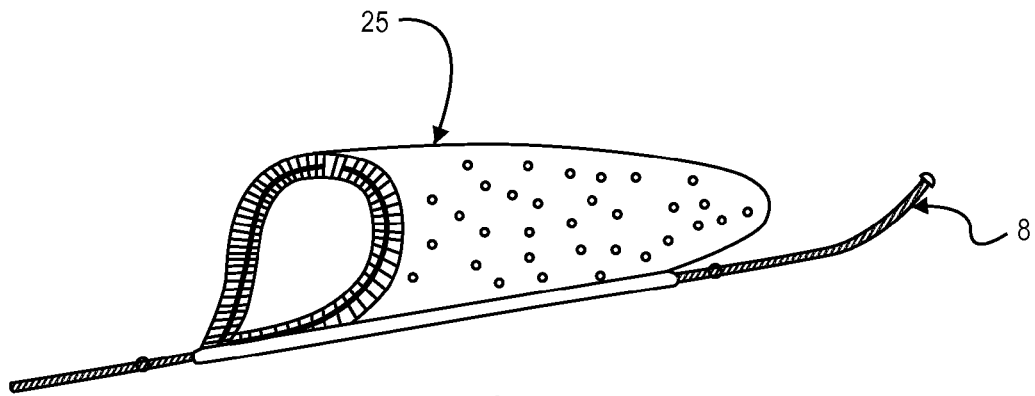
FIG. 18 illustrates other examples of filters where a loop style 25 has the guidewire passing along the side of the device and functions like a wind-sox when deployed in the vessel. The other example is a framed filter where when expanded the filter material is opposed to the vessel wall and the guidewire 8 passes through the central portion of the device.
Figure 18B:
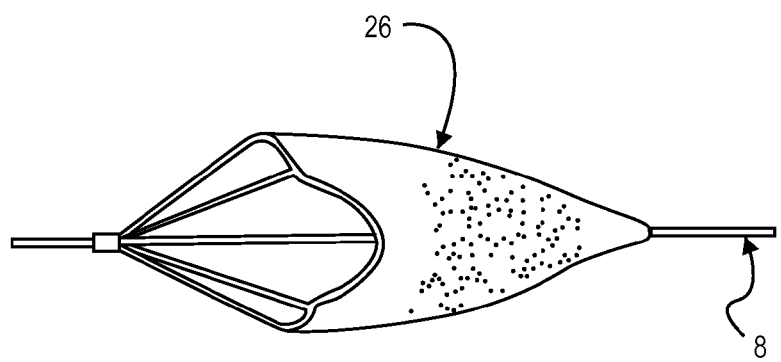
Figure 19:
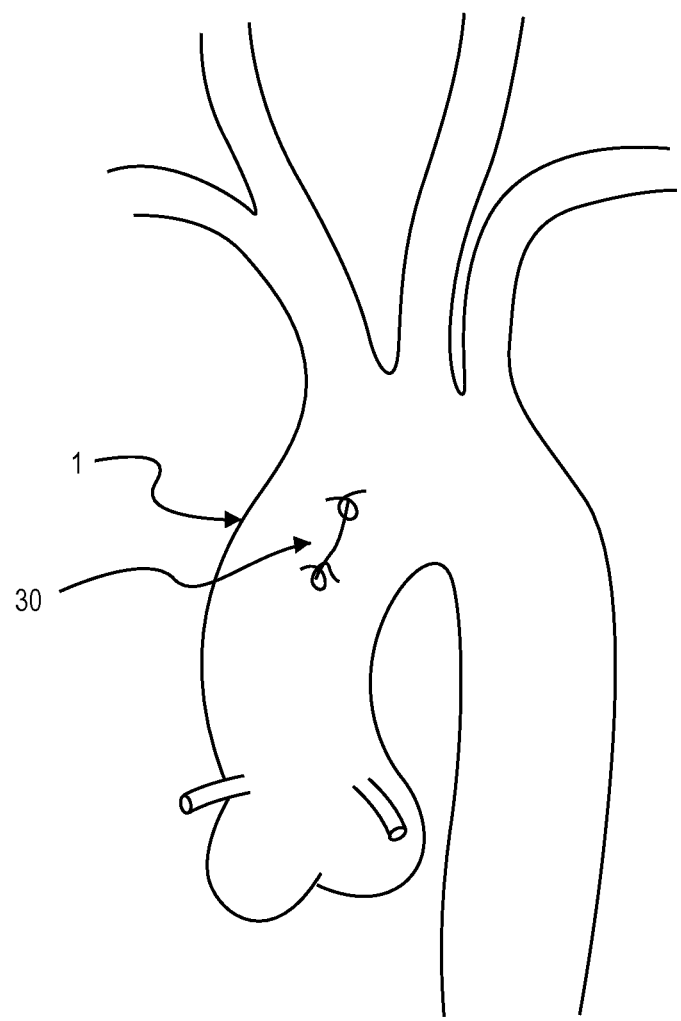
FIG. 19 illustrates a standard purse-string (30) suture in the aorta (1) to accept an aortic cannula for bypass surgery. The sutures are installed previous to the insertion of the cannula to tighten the suture around the cannula.
Figure 20:
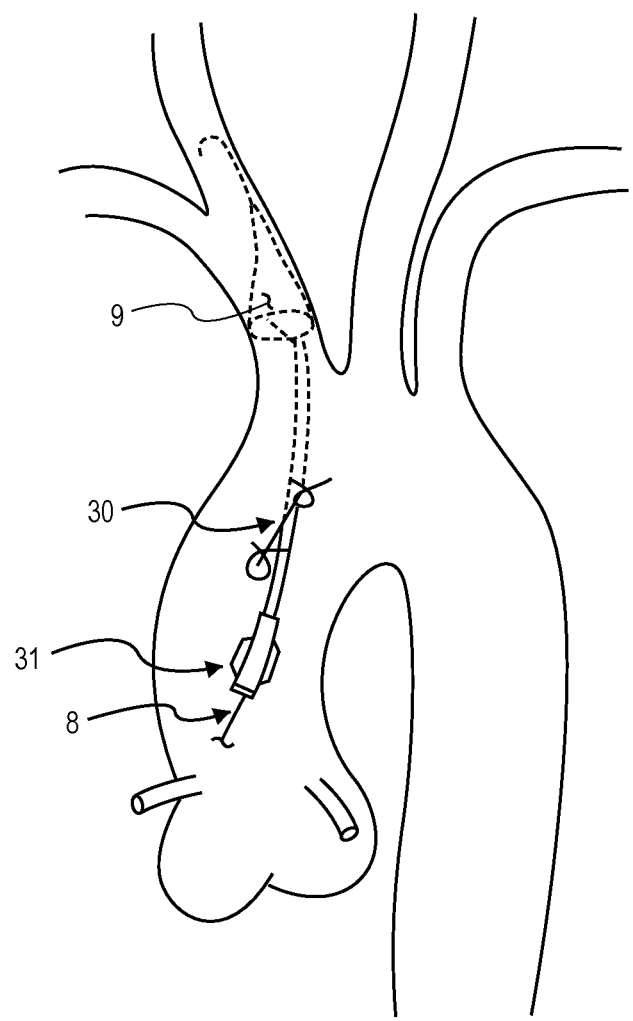
FIG. 20 illustrates an intravascular filter (9) inserted into the aorta between the purse-string sutures (30) with the aid of an introducer sheath (31). Exiting the sheath is the guidewire (8) to which the filter (9) is mounted.
Figure 21:
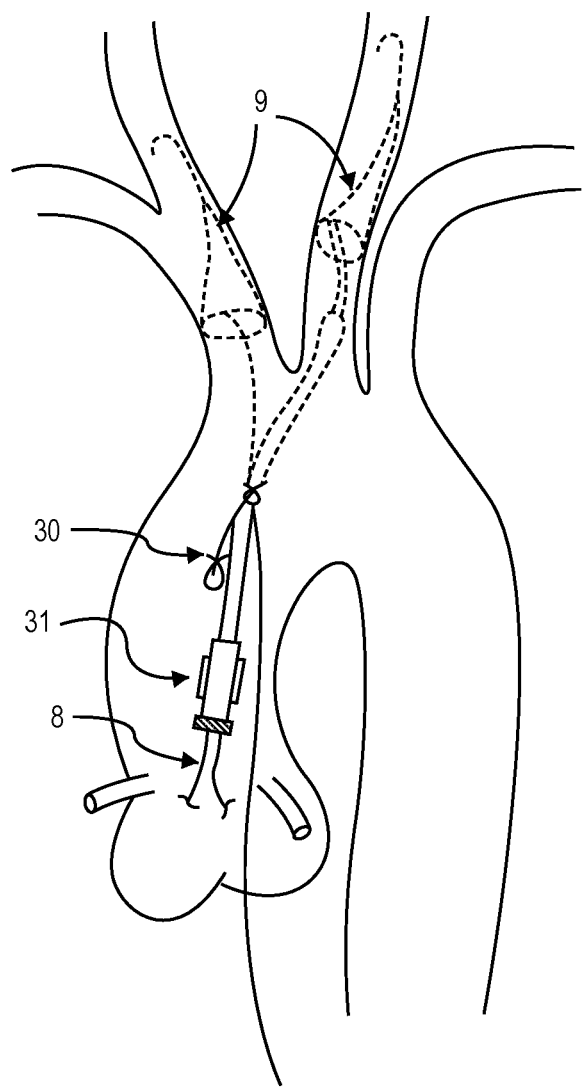
FIG. 21 illustrates two filters (9) inserted into the carotid arteries through a common introducer sheath (31) between the purse-string sutures (30) with the connecting guidewires (8) external to the body.
Figure 22:
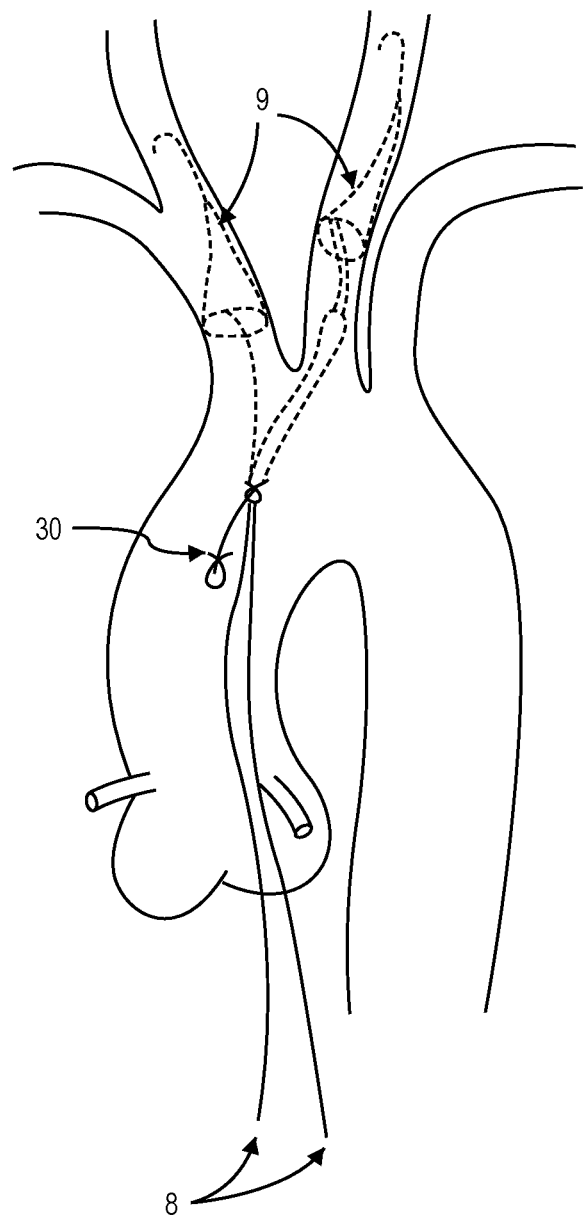
FIG. 22 illustrates the introducer sheath removed and the filters (9) in place tethered by two guidewires (8) exiting the aorta through the purse-string sutures.
Figure 23:
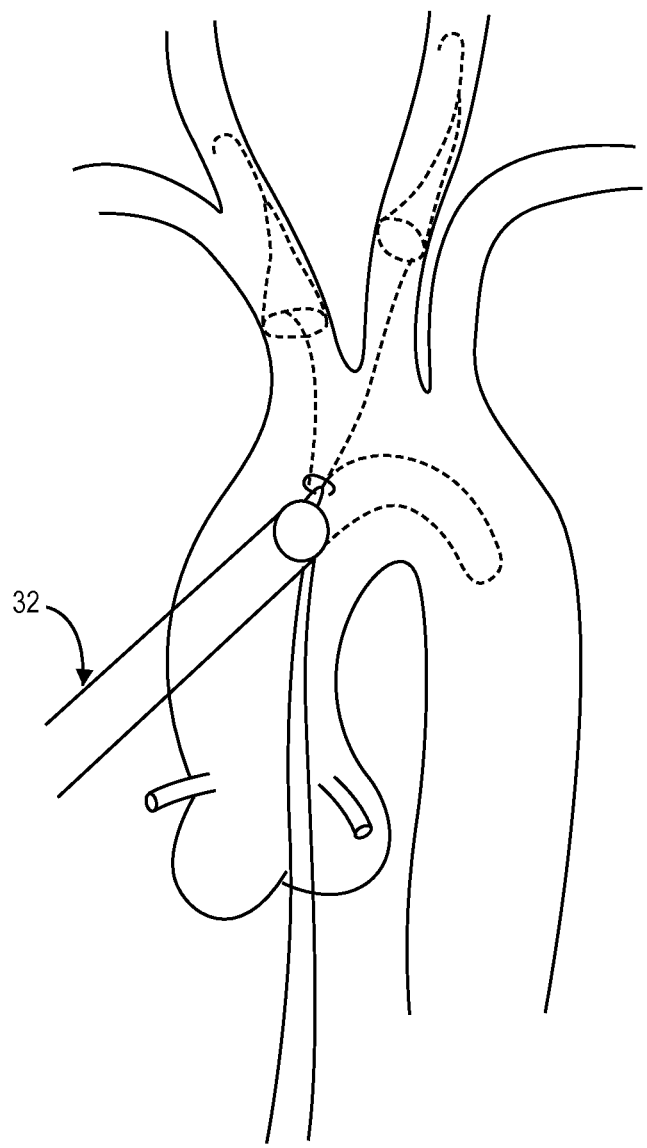
FIG. 23 illustrates the filters in the carotid arteries with the guidewires exiting the aorta and the aortic cannula (32) in place ready for perfusion. At this point the purse string-sutures would be tightened around the devices to limit blood loss and the cross-clamp can now be installed.
Figure 24:
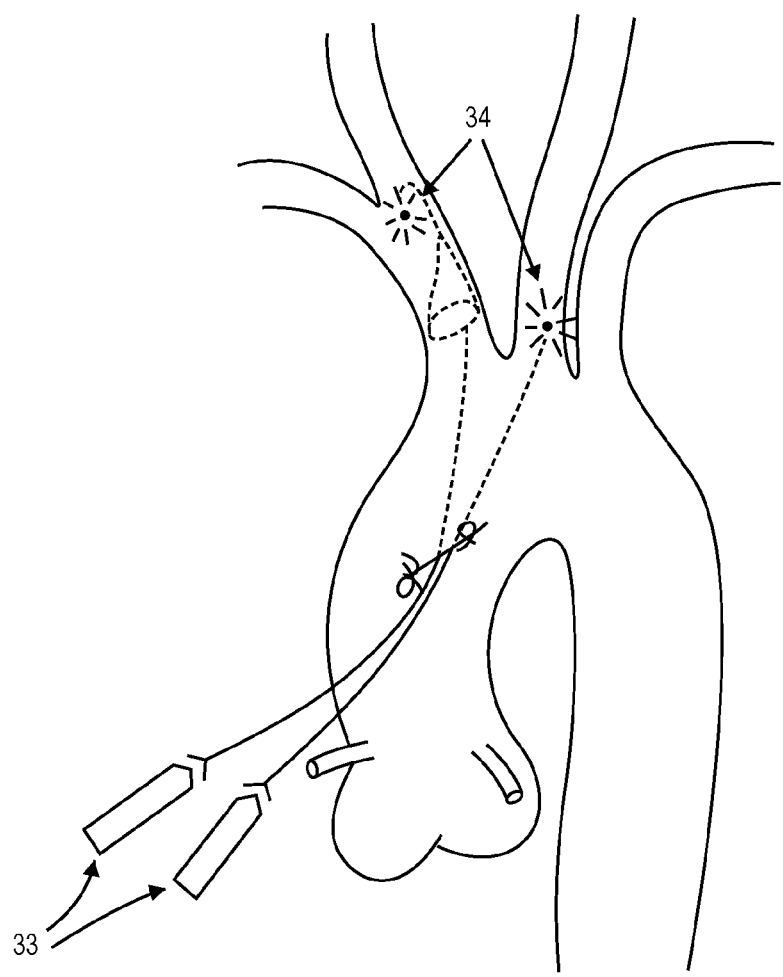
FIG. 24 illustrates the filters in place but with illumination wires (34) for visual guidance. External to the aorta is the illumination source (33) to deliver the light through the fiber.
Figure 25:
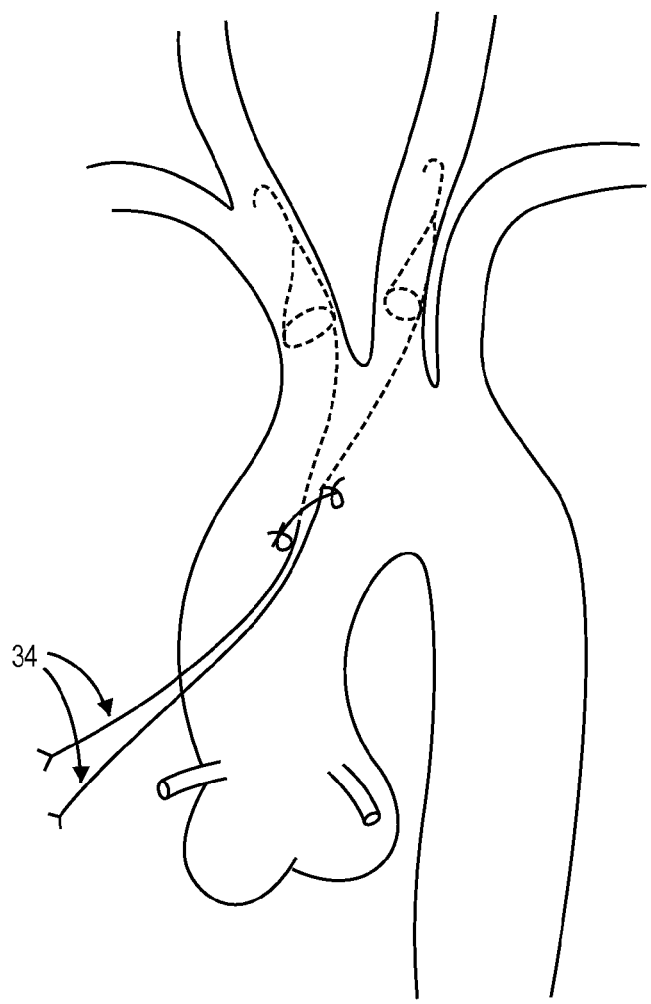
FIG. 25 illustrates the illumination sources disconnected from the guidewires (34) and removed from the sterile area for convenience. The filters are in the carotid arteries and now filtering any blood passing to the brain.
Figure 26:
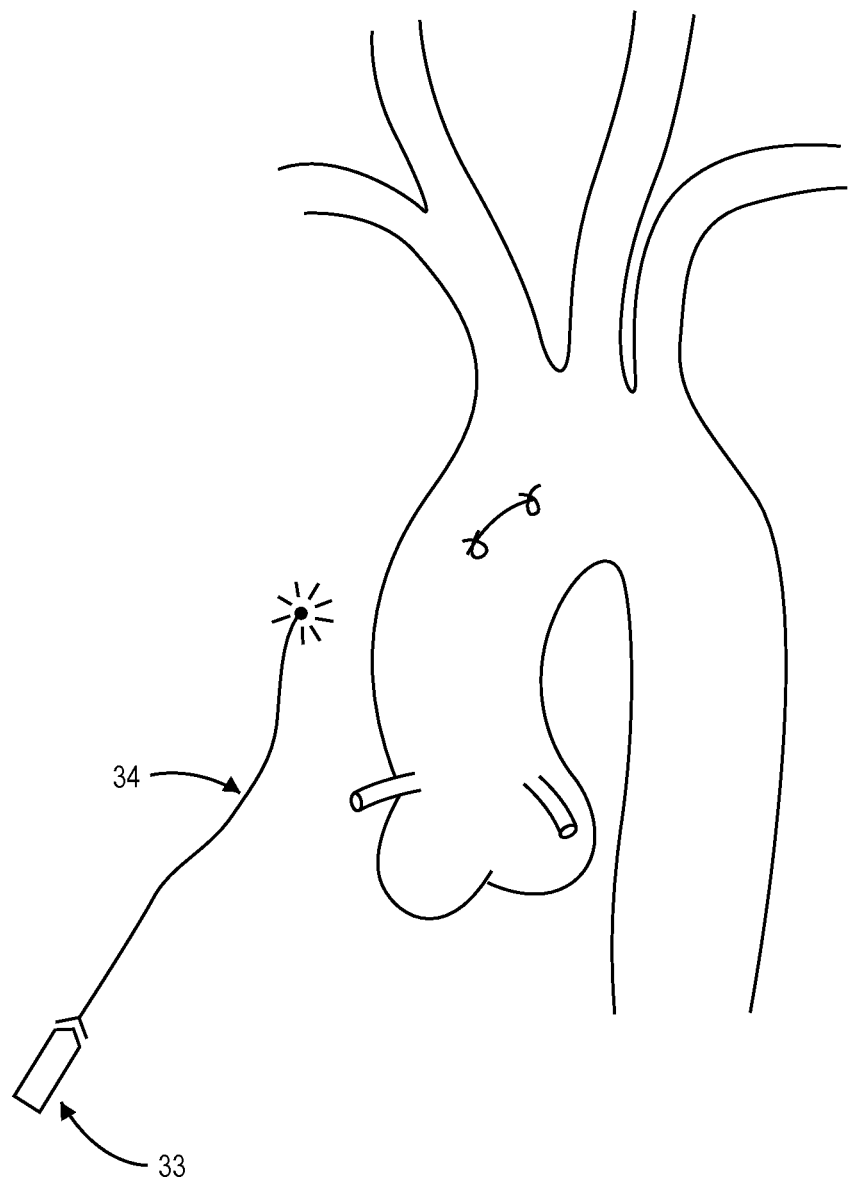
FIG. 26 illustrates the illumination guidewire (34) and illumination handle (33) external to the body ready for introduction through the purse-string sutures.
Figure 27:
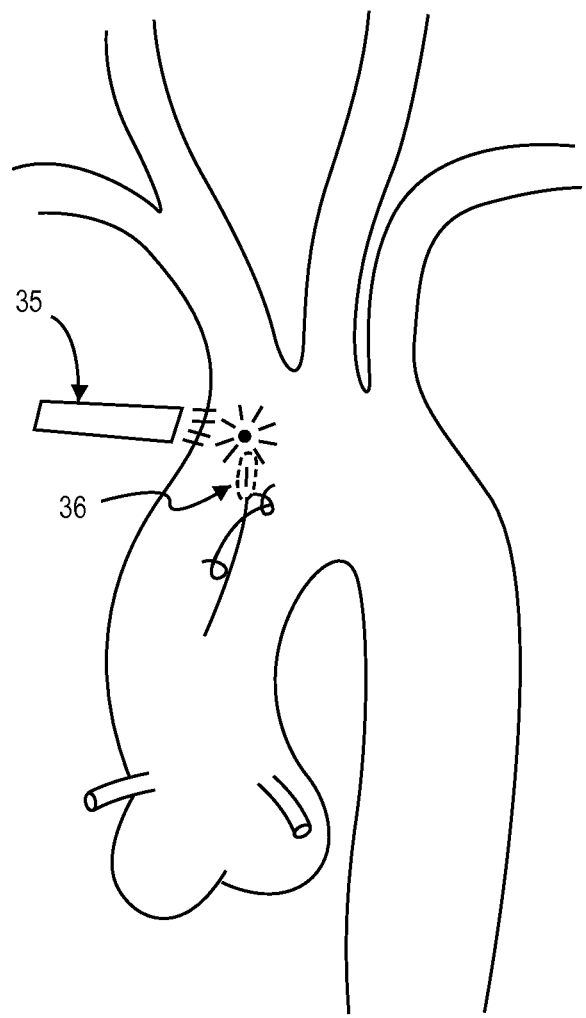
FIG. 27 illustrates an external magnet (35) being engaged to an internal magnet (36) to advance the filter into the carotid artery.

The invention described herein is an intravascular filter introduced to the aorta at or near the aortic cannulation site.

The device would be illuminated for guidance and have a relatively short overall length (10 to 40 cm). Any of the common intravascular filter devices could be used to complete the filtration of the blood but would need to have an illumination of some portion to guide the delivery to the carotid vessels. Introduced through a purse-string suture, the devices would measure about 1 to 4 millimeters in diameter and be delivered through a 5 or 6 French introducer over a guidewire where the introduction site would be the same as the cannula introduction site between the purse string sutures. Sheathed in a delivery catheter the filters would be exposed to the vessel in a collapsed state and advanced out the end of the delivery catheter where they would expand either passively by a memory metal such as Nitinol or actively by a balloon expansion or other radial force means. Once in place in the carotid vessels the delivery catheter may be removed leaving the tethered guidewires in the aorta exiting out the cannulation site. Illumination means could be a fiber optical guidewire, catheter or filter device. The corewire within the guidewire could be used to deliver light to the device or the guidewire could be made in an unconventional means and be a fiber to deliver the light through the vessel wall. This fiber could measure about 0.010 to 0.035 inches in diameter and also be an adjunct to the normal guidewire where one is used for vessel guidance and the other is used visual illumination. The wire lengths would be about 10 to 50 centimeters long and use a light source to illuminate the fiber that may be decoupled from the light source at the proximal end of the device for convenience. Once the surgical procedure is completed, the heart would be restarted and the cannulas removed stabilizing the patient ensuring the heart is free from arrhythmia and in good sinus rhythm. The filters may now be recovered and removed from the patients carotid vessels through the aorta. A recovery catheter would be advanced over the tethered guidewire where the filter is attached in the carotid artery. Collapsing the filter to a reduced size and pulling it into the recovery catheter will trap any emboli that may have occluded the distal vasculature and given the patient a stroke. Once in the recovery catheter the filters may be removed from the vessel and the patient will recover with a lower chance of stroke than if the procedure would have been completed without filtration.

Examples of these procedures include but are not limited to:

Coronary stenting
Aortic valve replacement via catheterization
Aortic or mitral valve replacement via transapical
Aortic balloon valvuloplasty
Mitral valvuloplasty
Mitral valve replacement via catheterization
Diagnostic catheterization
Surgical valve replacement (aortic or mitral)
Surgical valve repair (aortic or mitral)
Annuloplasty ring placement
Atrial fibrillation catheterization
PFO closure (surgical or catheter based)
Left atrial appendage closure (catheter or surgical)

Once the procedure has been completed the filters may be removed immediately or left in place if an antitrombotic coating is added or the patient remains on blood thinning agents to limit clot from forming on the filters. It may be advantageous to leave the filters in for a period of twenty-four hours as the patient begins to recover. When removal is necessary the goal is to not dislodge any trapped emboli within the filter. Conventionally this is accomplished by pulling the filter into a larger recovery sheath to first close the open end of the filter and draw the remaining portion safely back into the recovery catheter. With the filters being opposed in direction it may be advantageous to move the distal filter into the proximal filter and recover them both together in a nested orientation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of filtering a subject's blood to prevent foreign material from traveling into the carotid circulation during an open chest procedure, comprising
   creating an opening in an aorta prior to cross-clamping the aorta and cardiopulmonary bypass to provide access to the aorta;
   introducing a first illumination wire through the opening and into the left common carotid artery;
   introducing a first filter in a collapsed configuration through the opening and over the illumination wire;
   expanding the first filter in the left common carotid artery to trap foreign material in the left common carotid artery;
   introducing a second filter in a collapsed configuration through the opening;
   expanding the second filter in a brachiocephalic trunk to prevent foreign material from traveling into the right common carotid artery; and
   performing a procedure on the heart of the subject without expanding a filter within the aortic arch.

2. The method of claim 1, further comprising introducing a second illumination wire through the opening and into the brachiocephalic trunk.

3. The method of claim 2, further comprising advancing the second filter over the second illumination element and into the brachiocephalic trunk.

4. A method of filtering a subject's blood to prevent foreign material from traveling into the carotid circulation during an open chest procedure, comprising
   creating an opening in an aorta prior to cross-clamping the aorta and cardiopulmonary bypass to provide access to the aorta;
   advancing an introducer element through the opening and into the aorta;
   introducing a first filter in a collapsed configuration through the opening by advancing the first filter in the collapsed configuration through the introducer element;
   expanding the first filter in a left common carotid artery to trap foreign material in the left common carotid artery;
   introducing a second filter in a collapsed configuration through the opening by advancing the second filter in the collapsed configuration through the introducer element;
   expanding the second filter in a brachiocephalic trunk to prevent foreign material from traveling into the right common carotid artery;
   removing the introducer element from the opening in the aorta while leaving the first filter within the left common carotid artery and second filter in the brachiocephalic trunk; and performing a procedure on the heart of the subject without expanding a filter within the aortic arch.

5. The method of claim 4 further comprising the steps of after removing the introducing element from the opening in the aorta, inserting an aortic cannula for perfusion into the opening in the aorta, followed by the steps of cross-clamping the aorta and performing cardiopulmonary bypass.

6. A method of positioning a plurality of carotid circulation filters within a patient, comprising:
    creating an opening in an aorta to provide access through an introducer to the aorta prior to cardiopulmonary bypass;
    advancing an introducer through the opening and into the aorta;
    advancing a first illumination element through the introducer and into a left common carotid artery using illumination from the first illumination element as a visual positioning guide;
    advancing a second illumination element through the introducer and into a briachiocephalic trunk using illumination from the second illumination element as a visual positioning guide;
    advancing a first filter through the introducer and over the first illumination element and into the left common carotid artery using illumination from the first illumination element as a visual positioning guide;
    expanding the first filter in the left common carotid artery;
    advancing a second filter through the introducer and over the second illumination element and into the brachiocephalic trunk using illumination from the second illumination element as a visual positioning guide;
    expanding the second filter in the brachiocephalic trunk;
    removing the introducer from the opening and leaving the first and second illumination elements within the patient with a portion of the first and second illumination elements extending through the opening.

7. The method of claim 6 wherein the first illumination element comprises a guiding optical wire, the method further comprising advancing the first filter over the guiding optical wire into the left common carotid artery.

8. The method of claim 6 wherein the second illumination element comprises a guiding optical wire, the method further comprising advancing the second filter over the guiding optical wire into the brachiocephalic trunk.

9. The method of claim 6 further comprising introducing an aortic cannula through the opening.

10. The method of claim 6 further comprising positioning an introducer element through the opening, wherein the advancing steps comprise advancing the first and second illumination elements through the introducer element.

11. The method of claim 6 further comprising cross-clamping the aorta and performing cardiopulmonary bypass.

* * * * *

UNITED STATES PATENT AND TRADEMARK OFFICE
CERTIFICATE OF CORRECTION

| | | |
|---|---|---|
| PATENT NO. | : 8,518,073 B2 | Page 1 of 1 |
| APPLICATION NO. | : 12/696926 | |
| DATED | : August 27, 2013 | |
| INVENTOR(S) | : Lashinski | |

It is certified that error appears in the above-identified patent and that said Letters Patent is hereby corrected as shown below:

In the Specification

In column 2 at line 53 (approx.), Change "thromboemboli" to --thromboembolic--.

In column 5 at line 39, Change "and or" to --and/or--.

In column 6 at line 7, Change "savenous veign" to --saphenous vein--.

In column 9 at line 59, Change "antitrombotic" to --antithrombotic--.

In the Claims

In column 11 at line 20, In Claim 6, change "briachiocephalic" to --brachiocephalic--.

Signed and Sealed this
Twelfth Day of August, 2014

Michelle K. Lee
*Deputy Director of the United States Patent and Trademark Office*